(12) United States Patent
Palanker et al.

(10) Patent No.: US 8,043,286 B2
(45) Date of Patent: Oct. 25, 2011

(54) METHOD AND APPARATUS FOR PLASMA-MEDIATED THERMO-ELECTRICAL ABLATION

(75) Inventors: Daniel V. Palanker, Sunnyvale, CA (US); Alexander B. Vankov, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1094 days.

(21) Appl. No.: 11/784,382

(22) Filed: Apr. 6, 2007

(65) Prior Publication Data
US 2008/0039832 A1    Feb. 14, 2008

Related U.S. Application Data

(63) Continuation-in-part of application No. 10/825,716, filed on Apr. 16, 2004, now Pat. No. 7,238,185, which is a continuation of application No. 10/137,814, filed on May 3, 2002, now Pat. No. 6,780,178.

(51) Int. Cl.
A61B 18/18    (2006.01)
(52) U.S. Cl. ................. 606/34; 606/37; 606/41; 606/45
(58) Field of Classification Search .................... 606/34, 606/37
See application file for complete search history.

(56) References Cited

U.S. PATENT DOCUMENTS

| | | | |
|---|---|---|---|
| 3,799,168 A | 3/1974 | Peters | |
| 3,903,891 A | 9/1975 | Brayshaw | |
| 3,970,088 A | 7/1976 | Morrison | |
| 3,987,795 A | 10/1976 | Morrison | |
| 4,034,762 A | 7/1977 | Cosens et al. | |
| 4,043,342 A | 8/1977 | Morrison, Jr. | |
| 4,074,718 A | 2/1978 | Morrison, Jr. | |
| 4,161,950 A | 7/1979 | Doss et al. | |

(Continued)

FOREIGN PATENT DOCUMENTS

EA    0 697 841 B1    2/1996

(Continued)

OTHER PUBLICATIONS

Jones, H.M. et al. (Jan. 15,1995). "Pulsed Dielectric Breakdown of Pressurized Water and Salt Solutions," *J. Appl. Phys.* 77(2):795-805.

(Continued)

*Primary Examiner* — Linda Dvorak
*Assistant Examiner* — Jaymi Della
(74) *Attorney, Agent, or Firm* — Morrison & Foerster LLP

(57) ABSTRACT

Described herein are methods and apparatus for cutting a material including biological tissue. The apparatus has a cutting electrode with an elongate cutting portion. A voltage pulse waveform (typically comprising repeated bursts of minipulses) having a low or very low duty-cycle is applied to the cutting electrode to cut the tissue or other material by producing a vapor cavity around the cutting portion of the electrode and ionizing a gas inside the vapor cavity to produce a plasma. A low duty cycle cutting waveform may prevent heat accumulation in the tissue, reducing collateral thermal damage. The duration of the burst of minipulses typically ranges from 10 µs to 100 µs, and the rep rate typically ranges from 1 KHz to 10 Hz, as necessary. The apparatus and method of invention may cut biological tissue while decreasing bleeding and maintaining a very shallow zone of thermal damage.

21 Claims, 14 Drawing Sheets

U.S. PATENT DOCUMENTS

| | | |
|---|---|---|
| 4,202,337 A | 5/1980 | Hren et al. |
| 4,228,800 A | 10/1980 | Degler, Jr. et al. |
| 4,248,231 A | 2/1981 | Herczog et al. |
| 4,429,694 A | 2/1984 | McGreevy |
| 4,438,766 A * | 3/1984 | Bowers .................... 606/37 |
| 4,473,075 A * | 9/1984 | Rexroth .................... 606/37 |
| 4,476,862 A | 10/1984 | Pao |
| 4,492,231 A | 1/1985 | Auth |
| 4,534,347 A | 8/1985 | Taylor |
| 4,559,943 A | 12/1985 | Bowers |
| 4,589,411 A | 5/1986 | Friedman |
| 4,590,934 A | 5/1986 | Malis et al. |
| 4,593,691 A | 6/1986 | Lindstrom et al. |
| 4,597,388 A | 7/1986 | Koziol et al. |
| 4,655,215 A | 4/1987 | Pike |
| 4,674,499 A | 6/1987 | Pao |
| 4,682,596 A * | 7/1987 | Bales et al. ............. 606/39 |
| 4,781,175 A | 11/1988 | McGreevy et al. |
| 4,805,616 A | 2/1989 | Pao |
| 4,901,709 A | 2/1990 | Rattner et al. |
| 4,927,420 A | 5/1990 | Newkirk et al. |
| 4,936,301 A | 6/1990 | Rexroth et al. |
| 4,938,761 A | 7/1990 | Enssllin |
| 4,943,290 A | 7/1990 | Rexroth et al. |
| 5,080,660 A | 1/1992 | Buelna |
| 5,088,997 A | 2/1992 | Delahuerga et al. |
| 5,108,391 A | 4/1992 | Flachenecker et al. |
| RE33,925 E | 5/1992 | Bales et al. |
| 5,217,457 A | 6/1993 | Delahuerga et al. |
| 5,254,121 A | 10/1993 | Manevitz et al. |
| 5,267,994 A | 12/1993 | Gentelia et al. |
| 5,281,216 A | 1/1994 | Klicek |
| 5,300,068 A | 4/1994 | Rosar et al. |
| 5,318,563 A | 6/1994 | Malis et al. |
| 5,348,553 A | 9/1994 | Whitney |
| 5,423,814 A | 6/1995 | Zhu et al. |
| 5,454,809 A | 10/1995 | Janssen |
| 5,496,314 A | 3/1996 | Eggers |
| 5,549,604 A | 8/1996 | Sutcu et al. |
| 5,569,242 A | 10/1996 | Lax et al. |
| 5,599,346 A | 2/1997 | Edwards et al. |
| 5,647,871 A | 7/1997 | Levine et al. |
| 5,658,279 A | 8/1997 | Nardella et al. |
| 5,669,904 A | 9/1997 | Platt, Jr. et al. |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,766,153 A | 6/1998 | Eggers et al. |
| 5,766,170 A | 6/1998 | Eggers |
| 5,785,704 A | 7/1998 | Bille et al. |
| 5,843,019 A | 12/1998 | Eggers et al. |
| 5,860,976 A | 1/1999 | Billings et al. |
| 5,873,855 A | 2/1999 | Eggers et al. |
| 5,891,095 A | 4/1999 | Eggers et al. |
| 5,891,142 A | 4/1999 | Eggers et al. |
| 5,958,266 A | 9/1999 | Fugo et al. |
| 6,004,319 A | 12/1999 | Goble et al. |
| 6,032,674 A | 3/2000 | Eggers et al. |
| 6,047,700 A | 4/2000 | Eggers et al. |
| 6,053,172 A | 4/2000 | Hovda et al. |
| 6,056,746 A | 5/2000 | Goble et al. |
| 6,059,782 A | 5/2000 | Novak et al. |
| 6,059,783 A | 5/2000 | Kirwan, Jr. |
| 6,066,134 A | 5/2000 | Eggers et al. |
| 6,066,137 A | 5/2000 | Greep |
| 6,102,046 A | 8/2000 | Weinstein et al. |
| 6,113,594 A | 9/2000 | Savage |
| 6,132,427 A | 10/2000 | Jones et al. |
| 6,135,998 A | 10/2000 | Palanker |
| 6,149,620 A | 11/2000 | Baker et al. |
| 6,149,646 A | 11/2000 | West, Jr. et al. |
| 6,165,175 A | 12/2000 | Wampler et al. |
| 6,174,309 B1 | 1/2001 | Wrublewski et al. |
| 6,183,469 B1 | 2/2001 | Thapliyal et al. |
| 6,190,381 B1 | 2/2001 | Olsen et al. |
| 6,210,404 B1 | 4/2001 | Shadduck |
| 6,228,081 B1 | 5/2001 | Goble |
| 6,228,082 B1 | 5/2001 | Baker et al. |
| 6,228,084 B1 | 5/2001 | Kirwan, Jr. |
| 6,254,600 B1 | 7/2001 | Willink et al. |
| 6,267,757 B1 | 7/2001 | Aita et al. |
| 6,287,305 B1 | 9/2001 | Heim et al. |
| 6,287,306 B1 | 9/2001 | Kroll et al. |
| 6,352,535 B1 | 3/2002 | Lewis et al. |
| 6,355,032 B1 | 3/2002 | Hovda et al. |
| 6,358,248 B1 | 3/2002 | Mulier et al. |
| 6,364,877 B1 | 4/2002 | Goble et al. |
| 6,398,779 B1 | 6/2002 | Buysse et al. |
| 6,447,511 B1 | 9/2002 | Slater |
| 6,458,121 B1 | 10/2002 | Rosenstock et al. |
| 6,478,794 B1 | 11/2002 | Trapp et al. |
| 6,479,785 B1 | 11/2002 | Fugo et al. |
| 6,482,201 B1 | 11/2002 | Olsen et al. |
| 6,482,205 B1 | 11/2002 | Bonnet |
| 6,500,176 B1 | 12/2002 | Truckai et al. |
| 6,530,924 B1 | 3/2003 | Ellman et al. |
| 6,533,781 B2 | 3/2003 | Heim et al. |
| 6,544,261 B2 | 4/2003 | Ellsberry et al. |
| 6,589,237 B2 | 7/2003 | Woloszko et al. |
| 6,620,160 B2 | 9/2003 | Lewis et al. |
| 6,679,269 B2 | 1/2004 | Swanson |
| 6,726,683 B1 | 4/2004 | Shaw |
| 6,749,608 B2 | 6/2004 | Garito et al. |
| 6,770,071 B2 | 8/2004 | Woloszko et al. |
| 6,780,178 B2 | 8/2004 | Palanker et al. |
| 6,787,730 B2 | 9/2004 | Coccio et al. |
| 6,802,842 B2 | 10/2004 | Ellman et al. |
| 6,818,102 B1 | 11/2004 | Viol |
| 6,837,887 B2 | 1/2005 | Woloszko et al. |
| 6,949,096 B2 | 9/2005 | Davison et al. |
| 6,960,204 B2 | 11/2005 | Eggers et al. |
| 6,991,631 B2 | 1/2006 | Woloszko et al. |
| 7,004,941 B2 | 2/2006 | Tvinnereim et al. |
| 7,090,672 B2 | 8/2006 | Underwood et al. |
| 7,094,215 B2 | 8/2006 | Davison et al. |
| RE39,358 E | 10/2006 | Goble |
| 7,115,139 B2 | 10/2006 | McClurken et al. |
| 7,131,969 B1 | 11/2006 | Hovda et al. |
| 7,169,143 B2 | 1/2007 | Eggers et al. |
| 7,179,255 B2 | 2/2007 | Lettice et al. |
| 7,182,762 B2 | 2/2007 | Bortkiewicz |
| 7,186,234 B2 | 3/2007 | Dahla et al. |
| 7,192,428 B2 | 3/2007 | Eggers et al. |
| 7,195,627 B2 | 3/2007 | Amoah et al. |
| 7,195,630 B2 | 3/2007 | Ciarrocca |
| 7,201,750 B1 | 4/2007 | Eggers et al. |
| 7,238,185 B2 | 7/2007 | Palanker et al. |
| 7,270,658 B2 | 9/2007 | Woloszko et al. |
| 7,270,661 B2 | 9/2007 | Dahla et al. |
| 7,276,063 B2 | 10/2007 | Davison et al. |
| 7,357,802 B2 | 4/2008 | Palanker et al. |
| 7,429,262 B2 | 9/2008 | Woloszko et al. |
| 7,435,247 B2 | 10/2008 | Woloszko et al. |
| 7,445,618 B2 | 11/2008 | Eggers et al. |
| 7,468,059 B2 | 12/2008 | Eggers et al. |
| 7,736,361 B2 | 6/2010 | Palanker et al. |
| 7,789,879 B2 | 9/2010 | Palanker et al. |
| 2001/0012934 A1 | 8/2001 | Chandrasekaran et al. |
| 2001/0025177 A1 * | 9/2001 | Woloszko et al. .............. 606/41 |
| 2001/0034519 A1 | 10/2001 | Goble et al. |
| 2002/0026186 A1 | 2/2002 | Woloszko et al. |
| 2002/0052599 A1 | 5/2002 | Goble et al. |
| 2002/0052600 A1 | 5/2002 | Davison et al. |
| 2003/0069573 A1 * | 4/2003 | Kadhiresan et al. ............ 606/41 |
| 2004/0138654 A1 * | 7/2004 | Goble .............................. 606/34 |
| 2004/0162554 A1 | 8/2004 | Lee et al. |
| 2004/0199157 A1 | 10/2004 | Palanker et al. |
| 2004/0236321 A1 | 11/2004 | Palanker et al. |
| 2004/0267254 A1 | 12/2004 | Manzo et al. |
| 2005/0021028 A1 | 1/2005 | Palanker et al. |
| 2005/0177150 A1 * | 8/2005 | Amoah et al. .................. 606/34 |
| 2005/0220674 A1 | 10/2005 | Shafirstein et al. |
| 2005/0234439 A1 | 10/2005 | Underwood |
| 2005/0234446 A1 | 10/2005 | Van Wyk et al. |

| | | | |
|---|---|---|---|
| 2005/0288665 A1 | 12/2005 | Woloszko |
| 2006/0069386 A1 | 3/2006 | Dubnack et al. |
| 2006/0155270 A1 | 7/2006 | Hancock et al. |
| 2006/0253117 A1 | 11/2006 | Hovda et al. |
| 2006/0259025 A1 | 11/2006 | Dahla |
| 2006/0259033 A1 | 11/2006 | Nesbitt |
| 2007/0112348 A1 | 5/2007 | Eggers et al. |
| 2007/0129715 A1 | 6/2007 | Eggers et al. |
| 2007/0149966 A1 | 6/2007 | Dahla et al. |
| 2007/0179497 A1 | 8/2007 | Eggers et al. |
| 2007/0239156 A1 | 10/2007 | Palanker et al. |
| 2008/0004621 A1 | 1/2008 | Dahla et al. |
| 2008/0015565 A1 | 1/2008 | Davison |
| 2008/0021447 A1 | 1/2008 | Davison |
| 2008/0027428 A1 | 1/2008 | Palanker et al. |
| 2008/0039832 A1 | 2/2008 | Palanker et al. |
| 2008/0119842 A1 | 5/2008 | Palanker et al. |
| 2008/0125774 A1 | 5/2008 | Palanker et al. |
| 2008/0140066 A1* | 6/2008 | Davison et al. .................. 606/37 |
| 2009/0306642 A1 | 12/2009 | Vankov |

FOREIGN PATENT DOCUMENTS

| | | |
|---|---|---|
| EA | 0 697 841 B2 | 2/1996 |
| EA | 1 080 694 A1 | 3/2001 |
| EP | 0 012 037 A1 | 6/1980 |
| EP | 0 672 841 A2 | 9/1995 |
| EP | 0 672 841 A3 | 9/1995 |
| EP | 0 672 841 B1 | 9/1995 |
| EP | 0 694 290 B1 | 1/1996 |
| EP | 0 708 618 B1 | 5/1996 |
| EP | 0 754 437 A3 | 1/1997 |
| EP | 0 754 437 B1 | 1/1997 |
| EP | 0 754 437 B2 | 1/1997 |
| EP | 0 771 176 B1 | 5/1997 |
| EP | 0 771 176 B2 | 5/1997 |
| EP | 0 820 249 B1 | 1/1998 |
| EP | 0 833 593 B1 | 4/1998 |
| EP | 0 833 593 B2 | 4/1998 |
| EP | 0 837 647 B1 | 4/1998 |
| EP | 0 858 295 B1 | 8/1998 |
| EP | 0 865 256 B1 | 9/1998 |
| EP | 0 869 742 B1 | 10/1998 |
| EP | 0 873 089 B1 | 10/1998 |
| EP | 0 882 430 A3 | 12/1998 |
| EP | 0 882 430 B1 | 12/1998 |
| EP | 0 886 493 B1 | 12/1998 |
| EP | 0 887 046 B1 | 12/1998 |
| EP | 0 923 907 A1 | 6/1999 |
| EP | 0 949 886 B1 | 10/1999 |
| EP | 0 959 784 B1 | 12/1999 |
| EP | 0 959 786 B1 | 12/1999 |
| EP | 0 959 787 B1 | 12/1999 |
| EP | 0 996 378 B1 | 5/2000 |
| EP | 1 018 994 B1 | 7/2000 |
| EP | 1 025 807 A3 | 8/2000 |
| EP | 1 025 807 B1 | 8/2000 |
| EP | 1 026 996 B1 | 8/2000 |
| EP | 1 027 020 B1 | 8/2000 |
| EP | 1 034 746 A3 | 9/2000 |
| EP | 1 034 746 B1 | 9/2000 |
| EP | 1 034 747 A1 | 9/2000 |
| EP | 1 034 748 A1 | 9/2000 |
| EP | 1 036 547 A2 | 9/2000 |
| EP | 1 036 547 A3 | 9/2000 |
| EP | 1 039 862 B1 | 10/2000 |
| EP | 1 041 933 B1 | 10/2000 |
| EP | 1 050 278 A1 | 11/2000 |
| EP | 1 053 719 A1 | 11/2000 |
| EP | 1 053 720 A1 | 11/2000 |
| EP | 1 055 399 A1 | 11/2000 |
| EP | 1 061 857 B1 | 12/2000 |
| EP | 1 065 981 B1 | 1/2001 |
| EP | 1 079 746 B1 | 3/2001 |
| EP | 1 080 680 A1 | 3/2001 |
| EP | 1 082 944 B1 | 3/2001 |
| EP | 1 158 917 B1 | 12/2001 |
| EP | 1 174 093 A1 | 1/2002 |
| EP | 1 179 320 A2 | 2/2002 |
| EP | 1 179 320 A3 | 2/2002 |
| EP | 1 205 155 A1 | 5/2002 |
| EP | 1 253 866 B1 | 11/2002 |
| EP | 1 257 220 B1 | 11/2002 |
| EP | 1 287 788 A1 | 3/2003 |
| EP | 1 330 201 B1 | 7/2003 |
| EP | 1 330 989 B1 | 7/2003 |
| EP | 1 344 498 B1 | 9/2003 |
| EP | 1 374 788 A1 | 1/2004 |
| EP | 1 407 719 A3 | 4/2004 |
| EP | 1 581 128 B1 | 10/2005 |
| EP | 1 599 146 B1 | 11/2005 |
| EP | 1 632 191 A3 | 3/2006 |
| EP | 1 637 087 A3 | 3/2006 |
| EP | 1 693 015 A2 | 8/2006 |
| EP | 1 782 741 A3 | 5/2007 |
| EP | 1 880 686 A2 | 1/2008 |
| JP | 2001-178740 A | 7/2001 |
| WO | WO-96/39914 A1 | 12/1996 |
| WO | WO-97/27893 A1 | 8/1997 |
| WO | WO-97/48346 A1 | 12/1997 |
| WO | WO-98/03117 A1 | 1/1998 |
| WO | WO-98/03220 A1 | 1/1998 |
| WO | WO-98/19625 A2 | 5/1998 |
| WO | WO-98/19625 A3 | 5/1998 |
| WO | WO-98/56324 A1 | 12/1998 |
| WO | WO-99/03407 A1 | 1/1999 |
| WO | WO-99/03408 A1 | 1/1999 |
| WO | WO-99/03409 A1 | 1/1999 |
| WO | WO-99/09919 A1 | 3/1999 |
| WO | WO-99/16359 A1 | 4/1999 |
| WO | WO-99/20213 A1 | 4/1999 |
| WO | WO-99/30655 A1 | 6/1999 |
| WO | WO-99/32042 A1 | 7/1999 |
| WO | WO-99/40858 A1 | 8/1999 |
| WO | WO-99/49799 A1 | 10/1999 |
| WO | WO-00/09053 A1 | 2/2000 |
| WO | WO-00/41638 A1 | 7/2000 |
| WO | WO-00/54683 A1 | 9/2000 |
| WO | WO 00/62685 A1 | 10/2000 |
| WO | WO-00/62698 A1 | 10/2000 |
| WO | WO-00/62698 C1 | 10/2000 |
| WO | WO-00/71043 A1 | 11/2000 |
| WO | WO-01/35845 A1 | 5/2001 |
| WO | WO-01/60273 A1 | 8/2001 |
| WO | WO 01/95819 A1 | 12/2001 |
| WO | WO 02/11635 A1 | 2/2002 |
| WO | WO-02/19932 A1 | 3/2002 |
| WO | WO 03/092521 A1 | 11/2002 |
| WO | WO-02/102255 A1 | 12/2002 |
| WO | WO-03/005882 A2 | 1/2003 |
| WO | WO-03/005882 A3 | 1/2003 |
| WO | WO-03/024305 A2 | 3/2003 |
| WO | WO-03/024305 A3 | 3/2003 |
| WO | WO-03/024339 A1 | 3/2003 |
| WO | WO-03/028542 A2 | 4/2003 |
| WO | WO-03/028542 A3 | 4/2003 |
| WO | WO-03/068311 A2 | 8/2003 |
| WO | WO-03/068311 A3 | 8/2003 |
| WO | WO-03/090638 A1 | 11/2003 |
| WO | WO-2004/002293 A2 | 1/2004 |
| WO | WO-2004/002293 A3 | 1/2004 |
| WO | WO-2004/022155 A2 | 3/2004 |
| WO | WO-2004/022155 A3 | 3/2004 |
| WO | WO-2004/071278 A2 | 8/2004 |
| WO | WO-2004/071278 A3 | 8/2004 |
| WO | WO-2004/073752 A2 | 9/2004 |
| WO | WO-2004/073752 A3 | 9/2004 |
| WO | WO-2004/112581 A2 | 12/2004 |
| WO | WO-2004/112581 A3 | 12/2004 |
| WO | WO-2005/009213 A2 | 2/2005 |
| WO | WO-2005/009213 A3 | 2/2005 |
| WO | WO-2005/072634 A2 | 8/2005 |
| WO | WO-2005/072634 A3 | 8/2005 |
| WO | WO-2005/112806 A2 | 12/2005 |
| WO | WO-2005/112806 A3 | 12/2005 |
| WO | WO-2005/117735 A1 | 12/2005 |
| WO | WO-2005/122936 A1 | 12/2005 |
| WO | WO-2005/122938 A1 | 12/2005 |
| WO | WO-2006/002337 A2 | 1/2006 |

| | | | |
|---|---|---|---|
| WO | WO-2006/002337 | A3 | 1/2006 |
| WO | WO-2006/051252 | A1 | 5/2006 |
| WO | WO-2006/125007 | A2 | 11/2006 |
| WO | WO-2006/125007 | A3 | 11/2006 |
| WO | WO-2007/103800 | A2 | 9/2007 |
| WO | WO-2007/103800 | A3 | 9/2007 |
| WO | WO-2007/103800 | C1 | 9/2007 |
| WO | WO-2007/143445 | A2 | 12/2007 |
| WO | WO-2007/143445 | A3 | 12/2007 |

OTHER PUBLICATIONS

Jones, H.M. et al. (1995). "Development of Pulsed Dielectric Breakdown in Liquids," *J. Phys. D: Appl. Phys.* 28:178-188.

Palanker, D. et al. (2002). "Effect of the Probe Geometry on Dynamics of Cavitation," *Proc. SPIE* 4617:112-117.

Cushing, H. (Dec. 1928). "Electro-Surgery as an aid to the Removal of Intracranial Tumors," *Surgery, Gynecology and Obstetrics Magazine* XLVII(65):751-784.

European Examination Report mailed on Dec. 12, 2008, for EP Application No. 04755740.0 filed on Jun. 18, 2004, four pages.

European Search Report mailed on Jul. 18, 2007, for EP Application No. 04755740.0 filed on Jun. 18, 2004, four pages.

International Preliminary Report on Patentability mailed on Oct. 15, 2009, for PCT Application No. PCT/US2008/004460, filed on Apr. 4, 2008, six pages.

International Preliminary Report on Patentability mailed on May 14, 2009, for PCT Application No. PCT/US2007/023130, filed on Nov. 1, 2007, seven pages.

International Search Report and Written Opinion mailed on May 15, 2008, for PCT Application PCT/US2007/023130, filed on Nov. 1, 2007, eight pages.

International Search Report and Written Opinion mailed on Dec. 8, 2005, for PCT Application No. PCT/US04/19785, filed on Jun. 18, 2004, one page.

Miller, J.M. et al. (Jun. 2003). "Precision and Safety of the Pulsed Electron Avalanche Knife in Vitrecoretinal Surgery," *Arch Opthalmol* 121:871-877.

Mylrea, K.C. et al. (Jul.-Sep. 1981). "Introduction to Electrosurgery," *Journal of Clinical Engineering* 6(3):185-191.

U.S. Appl. No. 11/787,500, filed Apr. 16, 2007, by Palanker et al.

Palanker, D. et al. (Jun. 1, 1997). "Electrical Alternative to Pulsed Fiber-delivered Lasers in Microsurgery," *J. Appl. Phys.* 81(11):7673-7680.

Partial European Search Report mailed on Jul. 3, 2008, for EP Application No. 04 71 1134, filed on Sep. 14, 2005, five pages.

European Examination Report mailed on Sep. 2, 2010, for EP Application No. 03733930.6, filed on May 2, 2003, six pages.

Written Opinion mailed on May 15, 2008, for PCT Application No. PCT/US2007/023130, filed on Nov. 1, 2007, five pages.

Written Opinion mailed on Dec. 8, 2005, for PCT Application No. PCT/US04/19785, filed on Jun. 18, 2004, three pages.

\* cited by examiner

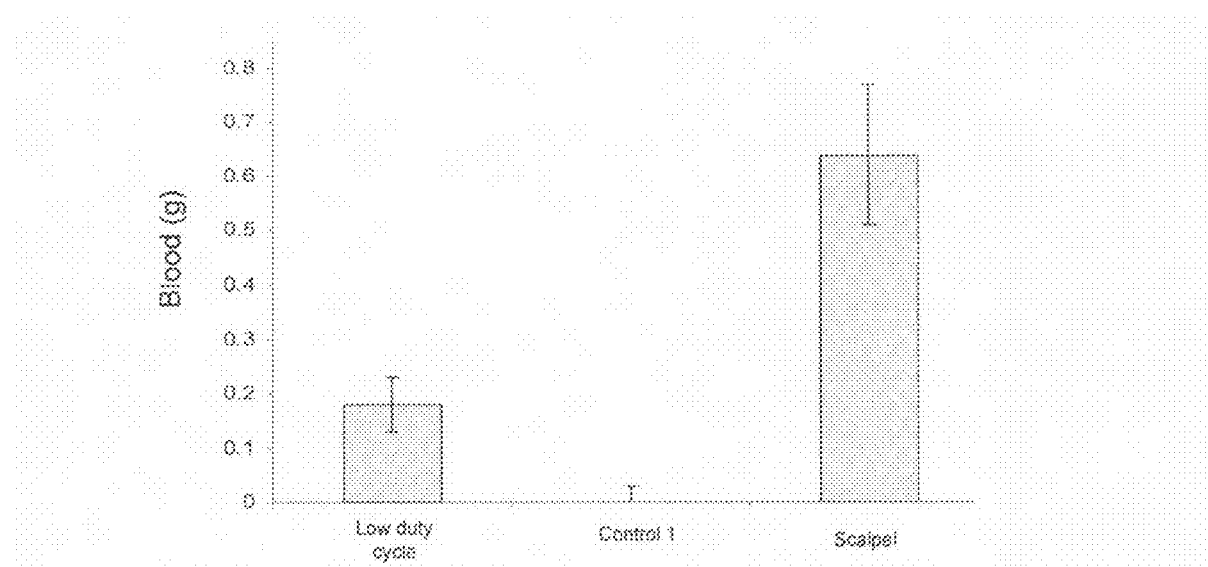
FIG. 16B
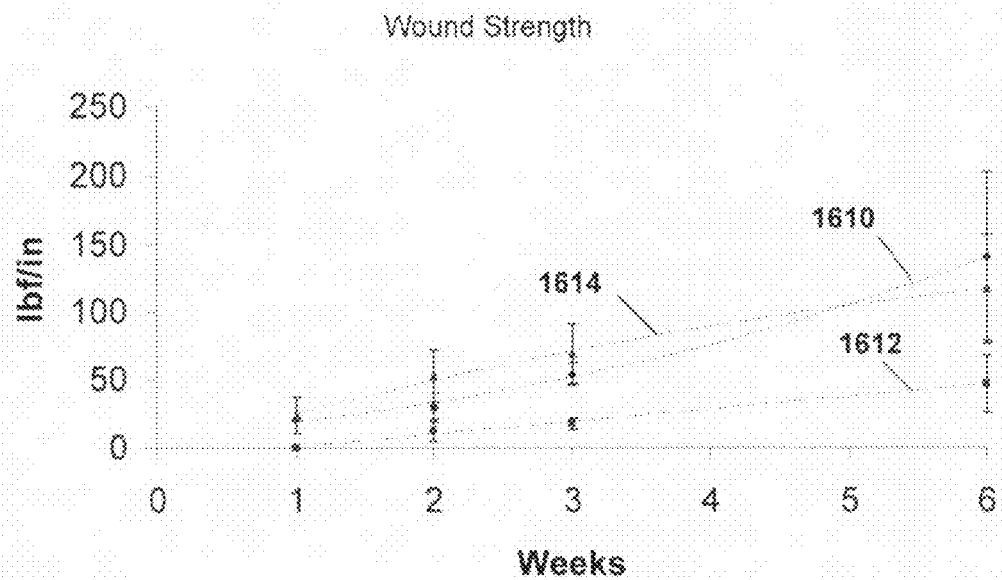

METHOD AND APPARATUS FOR PLASMA-MEDIATED THERMO-ELECTRICAL ABLATION

CROSS-REFERENCE TO RELATED APPLICATIONS

This application is a Continuation-in-Part of U.S. application Ser. No. 10/825,716, filed on Apr. 16, 2004, which issued as U.S. Pat. No. 7,238,185 and which is a Continuation of U.S. application Ser. No. 10/137,814, filed May 3, 2002, which issued as U.S. Pat. No. 6,780,178. All of these applications and issued patents are herein incorporated by reference in their entirety.

STATEMENT REGARDING FEDERALLY SPONSORED RESEARCH OR DEVELOPMENT

This invention was supported by the National Institutes of Health under contract number RO1 EY 12888-02. The government has certain rights in this invention.

REFERENCE TO A COMPACT DISK APPENDIX

Not applicable.

FIELD OF THE INVENTION

The present invention relates to an apparatus for cutting materials including biological tissue by thermo-electrical ablation with the aid of a plasma produced around a cutting electrode and to a method for driving such electrode with appropriate pulses.

BACKGROUND

The cutting of materials with the aid of cutting electrodes energized by a suitable power source is a known technique that is being successfully employed, e.g., in the field of electrosurgery. Typical electrosurgical devices apply an electrical potential difference or a voltage difference between a cutting electrode and a patient's grounded body (monopolar arrangement) or between a cutting electrode and a return electrode (bipolar arrangement) to deliver electrical energy to the area where tissue is to be cut. The voltage is applied either as a continuous train of high frequency pulses, typically in the RF range, or as direct current (DC).

The prior art provides a number of exemplary designs of bipolar electrosurgical electrodes. For example, U.S. Pat. No. 5,108,391 describes a bipolar treating apparatus with a first active electrode and a second return electrode having exposed distal ends to define a bipolar tip for electrosurgically treating tissue. U.S. Pat. No. 5,700,262 describes a bipolar electrode with fluid channels for performing neurosurgery. Additional information about bipolar electrosurgical devices and knives can be found, e.g., in U.S. Pat. Nos. 4,202,337 and 4,228,800 as well as numerous other open literature sources.

Depending on the conditions, the application of a voltage to a monopolar electrode or between the cutting and return electrodes of a bipolar electrode produces a number of physical phenomena. Most prior art devices take advantage of one of these phenomena to perform the cut. In particular, one class of devices uses a gas stream that is generated around the cutting electrode. For example, U.S. Pat. No. 5,217,457 describes an electrosurgical apparatus using a stream of gas that shrouds the electrode and an electrosurgical apparatus incorporating this electrode for cutting biological tissue. U.S. Pat. No. 5,088,997 also teaches the use of a stream of gas for electrosurgical procedures for coagulating or cutting biological tissue. On the other hand, U.S. Pat. No. 5,300,068 teaches an electrosurgical apparatus for cutting tissue and for ablating occlusions using arc discharges produced on a monopolar electrode in response to a train of pulses. Taking advantage of a yet different phenomenon, U.S. Pat. No. 6,352,535 teaches a method and device for electro microsurgery in a physiological liquid environment that uses high voltage electrical discharges of sub-microsecond duration in a liquid medium to produce cavitation bubbles. The cavitation bubbles have a size in the sub-millimeter range and are used for high-speed precision cutting with an inlaid disc electrode.

In addition to taking advantage of different phenomena to perform the cut, prior art devices employ various techniques for generating and applying the voltage to the electrode or electrodes. U.S. Pat. No. 6,135,998 teaches an electrosurgical device which uses extremely short monopolar voltage pulses, typically shorter than 200 ns, to drive an electrode having an inlaid disc geometry. This invention attempts to mitigate some of the negative cavitation effects, such as the damaging jets formed after the collapse of the cavitation bubble. U.S. Pat. No. 5,108,391 describes a high frequency generator for tissue cutting and for coagulating in high-frequency surgery. This device uses an electric arc discharge to perform the cutting operation. U.S. Pat. No. 6,267,757 teaches a device which uses radio-frequency (RF) ablation for revascularization. It employs a source, which delivers at least one burst of RF energy over an interval of about 1 to about 500 ms, and preferably about 30 to about 130 ms. This device has an elongated insulated, electrical conducting shaft with an uninsulated distal tip, which is configured to emit the RF energy. U.S. Pat. No. 6,364,877 also describes the use of high frequency pulses applied in a continuous manner. The teaching found in U.S. Pat. Nos. 5,697,090 and 5,766,153 suggests that a continuous train of high frequency pulses can be pulsed at a rate sufficient to allow the electrode to cool.

Unfortunately, despite all the above teachings, electrosurgical methods and apparatus generally suffer from an inability to control the depth of tissue damage (necrosis) in the tissue being treated. Most electrosurgical devices described above rely on a gas jet, an arc discharge or cavitation bubbles to cut, coagulate or ablate tissue. Such imprecise cutting methods cause tissue necrosis extending up to 1,700 μm into surrounding tissue in some cases.

In an effort to overcome at least some of the limitations of electrosurgery, laser apparatus have been developed for use in arthroscopic and other procedures. Lasers do not suffer from electrical shorting in conductive environments and certain types of lasers allow for very controlled cutting with limited depth of necrosis. U.S. Pat. No. 5,785,704 provides an example of a laser used for performing stereotactic laser surgery. Unfortunately, lasers suffer from limitations such as slow operating speed, inability to work in liquid environments, high cost, inconvenient delivery systems and other defects that prevent their more universal application. For these reasons, it would be desirable to provide improved apparatus and efficient methods for driving an electrosurgical apparatus for ablating tissue in a highly controlled and efficient manner while minimizing tissue damage.

The prior art has attempted to provide for more controlled electrosurgery by relying on plasma-mediated cutting and ablation of soft biological tissue in conductive liquid media at low temperatures. The fundamentals of this approach, which is used predominantly in the continuous pulse regime and various embodiments employing it, are described in the patents of Arthrocare including U.S. Pat. Nos. 5,683,366; 5,697, 281; 5,843,019; 5,873,855; 6,032,674; 6,102,046; 6,149,620; 6,228,082; 6,254,600 and 6,355,032. The mechanism of low temperature ablation is called "coblation" and is described as electric field-induced molecular breakdown of target tissue through molecular dissociation. In other words, the tissue structure is volumetrically removed through molecular disintegration of complex organic molecules into non-viable atoms and molecules, such as hydrogen, oxides of carbon, hydrocarbons and nitrogen compounds. This molecular disintegration completely removes the tissue structure, as opposed to transforming the tissue material from solid form directly to a gas form, as is typically the case with ablation (see U.S. Pat. No. 5,683,366). More specifically, this mechanism of ablation is described as being associated with two factors: (1) "photoablation" by UV light at 306-315 nm and visible light at 588-590 nm produced by the plasma discharge; and (2) energetic electrons (e.g. 4 to 5 eV) can subsequently bombard a molecule and break its bonds, dissociating a molecule into free radicals, which then combine into final gaseous or liquid species (see U.S. Pat. No. 5,683,366). Surface temperature of tissue in this process is maintained between 40-70° C. This type of ablation mechanism has low rate of tissue dissection and a very limited applicability to hard tissues such as, for example, bones.

Despite these new advances the electrosurgical techniques are still experiencing a number of problems remain. First and foremost, the amount of power required to operate the prior art cutting devices remains in a high range of several Watts which precludes applications of these devices to such delicate organs as an eye. Second, the devices exhibit large energy and heat losses. These high losses translated into excessive power deposition into the tissue being ablated. Additional heat losses to the hand piece are also substantial. Third, even the best prior art devices operating at the lowest power levels have difficulties cutting hard biomaterials like bones and non-conducting materials such as cellulose or plastics.

Increasingly sophisticated surgical procedures create a growing demand for more precise and less traumatic surgical devices. For example, the critical importance and delicate nature of the eye makes the demand for precision and safety of intraocular microsurgical instrumentation particularly important. For these and other reasons, it would be a major advance in the art to provide an apparatus and method for ablating materials at low power levels. It would be particularly useful to provide such apparatus and method that reduces heat losses to the material being cut as well as into the surroundings and, especially the hand piece. Furthermore, it would also be an advance to expand the range of materials that can be ablated to include biological tissue, cellulose and plastics.

OBJECTS AND ADVANTAGES

In view of the above shortcomings of the prior art, it is an object of the invention to produce a cutting apparatus and provide a method for operating it to achieve efficient thermal ablation at low power levels, e.g., ranging down to 10 mW, in various types of materials including biological tissue. Specifically, it is an aim of the invention to minimize the damage zone produced during the cutting process by using plasma-assisted cutting and minimizing heat losses into the material being cut as well as the surroundings and the hand piece.

It is another object of the invention to provide a modulation format or regime for pulsed operation of the cutting apparatus to minimize adverse effects in cutting biological tissue. In particular, it is one object of the invention to provide an electrosurgical cutting pulsing regime (also referred to as a pulsed waveform) that operates at low and very low duty-cycles.

It is yet another object of the invention to reduce the average temperature that the cutting apparatus acting on the biological tissue operates on during cutting.

Yet another object of the invention is to provide a versatile cutting electrode geometry for efficient cutting and removal of material. Some of these electrodes and the driving waveforms are specifically designed for applications specific types of surgery, including IMA and radial artery access and harvesting (cardiac surgeries), arthroscopy (sports medicine procedures); tonsillectomy (ENT surgeries); LEEP, abdominal hysterectomy (Ob/Gyn procedures); fusion, microdiscectomy (Neuro/Spinal procedures); intra and extra ocular procedures (Ophthalmology).

These and other objects and advantages will become apparent upon review of the following description and figures.

BRIEF SUMMARY OF THE INVENTION

The objects and advantages of the invention are achieved by a method for cutting a material including conducting and non-conducting materials such as biological tissue, cellulose or plastic. During cutting the material may be submerged in a conductive liquid medium. Dry cutting may also be performed. The method may involve providing a cutting electrode with an elongate cutting portion and a return electrode. The elongate cutting portion may have an aspect ratio of length to width larger than 1 and preferably larger than 5. A thin cutting electrode may allow for dissection of tissue with low energy deposition. A voltage is typically applied between the two electrodes so that the cutting electrode is heated to produce a vapor cavity around the elongate cutting portion and gas inside the vapor cavity is ionized to produce a plasma. The plasma may maintain the electrical conductivity between the electrodes. The voltage applied between the electrodes may be modulated in pulses having a modulation format selected to minimize the size of the vapor cavity, the rate of formation of the vapor cavity and heat diffusion into the material as the material is cut with an edge of the elongate cutting portion of the cutting electrode. The modulation format may be characterized as a low (or very low) duty-cycle pulse waveform.

The modulation format may include pulses having a pulse duration in the range from 10 µs to 10 µs. The pulses may be composed of minipulses having a minipulse duration in the range between 0.01 µs and 10 µs and an interval ranging from 0 to 10 µs between the minipulses. The minipulse duration may be selected from the range substantially between 0.2 and 5 µs and the interval between them is shorter than a lifetime of the vapor cavity. The peak power of the minipulses can be varied from minipulse to minipulse.

When the method is used for cutting biological tissue it may be preferable to use minipulses with alternating polarity, including bipolar minipulses, in which a minipulse has both negative and positive components. Thus, the modulation format may contain minipulses that exhibit alternating positive and negative polarities or both positive and negative polarities per pulse. This modulation format may limit the amount of charge transfer to the tissue and reduce or greatly minimize various adverse tissue reactions such as muscle contractions and electroporation. Additional devices for preventing charge transfer to the biological tissue may be employed in combination with this modulation format or separately when the method of invention is applied in performing electrosurgery.

In the same or in an alternative method of the invention the minipulses may be further made up of micropulses. When the modulation format includes micropulses it is preferred that they have a duration ranging between 0.1 and 1 μs.

It is well-known that spark discharges develop in advance of an arc discharge. In accordance with the invention it is preferable to adjust the modulation format to permit spark discharges while preventing arc discharges. For example, the modulation format such as minipulse duration and peak power may be adjusted to permit spark discharges while avoiding arc discharges. Furthermore, the voltage and the modulation format may be selected such that the temperature of the elongate cutting portion of the cutting electrode and of the plasma are maintained significantly above the boiling temperature of water. Preferably, the temperature of the elongate cutting portion is maintained between about 100 and 1,000° C. This temperature may be a peak temperature for the cutting electrode. The average (e.g., RMS) temperature may be substantially less than 100° C. For example, the average temperature of the cutting electrode (e.g., the exposed electrode surface of the cutting electrode) may be less than approximately 50° C. In some variations, the average temperature of the exposed cutting electrode surface is less than 40° C. (e.g., approximately 37° C.).

The apparatus and systems described herein may be equipped with the cutting electrode with the elongate cutting portion and a return electrode. A voltage source may be used for applying the voltage between the cutting and return electrodes to produce the vapor cavity with plasma. A pulse control may be provided for controlling the modulation format of the voltage applied between the electrodes. The pulse control may include a peak power control and a duration control for adjusting pulse power, pulse duration and pulse interval. Additional controls may be provided to control the pulsing waveform, including a control for repetition rate (e.g., repetition of bursts of minipulses), minipulse burst duration control, minipulse duration control, number of minipulses per burst, and voltage range applied (e.g., ±peak voltage). The pulse control may be limited to prevent application of a duty cycle above a threshold during a cutting pulsing waveform. For example the ranges provided to adjust any of the parameters given above may be limited so that the duty cycle of the pulsing waveform is below a certain value (e.g., 10%, 7%, 5%, 2.5%, 1%, etc.).

The shape, size, and length of the cutting electrode and the elongate cutting portion can vary according to the material being cut. For a number of electrosurgical applications the elongate cutting portion should have a width (or thickness) of between about 1 μm and 200 μm and preferably between 10 μm and 100 μm. The elongate cutting portion can have various cross sections including circular, e.g., it is in the form of a wire. In some variations, the entire cutting electrode can be in the form of a wire electrode. In some variations, a blade or edged cutting electrode (including an insulated region and an uninsulated edge) may be used. Examples of cutting electrode may be found in application including U.S. Ser. No. 10/779, 529, filed Feb. 13, 2004 (titled "Electrosurgcial System with Uniformly Enhanced Electric Field and Minimal Collateral Damage"), herein incorporated by reference in its entirety. The elongate cutting portion can have one or more bends or curves. For example, in certain electrosurgical applications the elongate cutting portion can be L-shaped or U-shaped. In some embodiments the elongate cutting portion can form a loop, e.g., it can be a looped wire electrode. In some embodiments it is advantageous to provide a device for advancing the wire electrode such that a length of the wire used for cutting can be adjusted during the application, when required. Such adjustment affects the impedance of the electrode and can be used for control of power dissipation. In addition, a fresh portion of the wire can be extended to replace the eroded portion. In one particular embodiment, the elongate cutting portion and the terminal portion of return electrode are both shaped into a shape suitable for capsulotomy.

In embodiments where transferring charge to the material should be avoided, e.g., when the material being cut is biological tissue, the apparatus or systems described herein may include a device for preventing charge transfer through the non-conducting material. For example, a circuit with a separating capacitor, e.g., an RC-circuit, can be used for this purpose.

The devices, system and methods described herein operate using a pulse waveform that has a low (to very low) duty cycle. This is unlike prior art electrosurgical cutting systems, which typically operate with continuous (e.g., between 100% to 50% duty cycle). For example, in traditional RF cutting, cutting is achieved by the accumulation of action over long time (i.e., long duty cycle). In continuous RF systems the duty cycle is approximately 1 (or 100%) during cutting. Other pulsed cutting waveforms may have slightly lower duty cycle, typically between approximately 0.5 (or 50%) and 0.3 or (30%). In contrast, the pulse waveforms described herein operate at a very low duty cycle (e.g., typically less than or equal to 0.1 or 10%).

Thus, methods for thermo-electrical cutting of biological tissue are described herein, including methods for the application of a low duty-cycle pulse waveform to a cutting electrode, wherein the cutting electrode is connected to a voltage control unit. Material (including a biological material) may then be cut with the cutting electrode during application of the low duty-cycle pulse waveform.

The low duty-cycle pulse waveform may include pulsing waveforms involving the application of a plurality of pulses having a duty cycle of less than about 10%, less than about 5%, and duty cycles of between about 2.5% and about 0.01%.

In some variations, the low duty-cycle cutting waveform comprises a plurality of pulses wherein each pulse comprises a burst of minipulses. Each burst of minipulses that make up a "pulse" is repeated with a repetition rate. For example, the repetition rate may be selected from between about 10 Hz and about 500 Hz, so that the time between bursts of minipulses (the "interburst repetition rate") may vary between 100 ms and 2 ms. The burst of minipulses typically have a duration between about 10 μs and 100 μs.

A burst of minipulses typically includes a plurality of minipulses (e.g., two or more minipulses per burst). Any appropriate number of pulses may be present, depending on the duration of each minipulse and the duration of the burst of minipulses. In some variations, each minipulse within the burst of minipulses has a duration of between about 10 ns to about 100 μs. The minipulses within the burst of minipulses may be bipolar minipulses. For example, alternating minipulses may have different polarities. In some variations, each individual minipulse is bipolar, and has a positive and a negative voltage component. The minipulses within the burst may be separated by a minipulse intraburst interval. For example, between 0 and 100 μs. In some variations, the minipulses within each burst of minipulses are continuously applied.

The voltage of the pulses (e.g., the minipulses) within a low duty-cycle cutting waveform may have any appropriate voltage. In variations in which the minipulses are bipolar, the voltage may vary between about −600 V and about +600 V, or between about −500 V and +500 V, or between about −400 V and +400 V.

As a consequence of the low duty-cycle activation of the cutting electrode, material heated during the pulse cools down between the pulses, thus the average temperature of the cutting electrode during cutting is typically less than 100° C., and may be less than 50° C., or less than 40° C. During application of a low duty-cycle pulse waveform, a plasma may be transiently formed along the edge of the cutting electrode. For example, a vapor cavity may be formed during the burst of minipulses, and the vapor cavity may be ionized. During the period between the bursts of minipulses, the temperature of the cutting electrode may cool or relax back down, so that the average temperature of the cutting electrode during cutting is much lower than the peak temperature during plasma formation. However, the peak temperature of the cutting electrode during cutting (e.g., along the cutting edge at the formation of plasma) may be greater than 100° C.

Described herein are methods for thermo-electrical cutting of biological tissue including the steps of applying a pulse waveform having a duty-cycle of less than 10% to a cutting electrode (wherein the pulse waveform comprises a plurality of bursts of minipulses having an interburst repetition rate of between about 10 Hz and 500 Hz, and a minipulse burst duration of between about 5 μs and about 200 μs or about 10 μs and about 100 μs), and cutting the tissue with the cutting electrode during application of the pulse waveform.

Also described herein are methods for thermo-electrical cutting of biological tissue including the steps of forming a plasma on a cutting electrode by applying a low duty-cycle pulse waveform (wherein the pulse waveform comprises a plurality of bursts of minipulses having an interburst repetition rate of between about 10 Hz and 500 Hz, and a minipulse burst duration of between about 5 μs and about 200 μs or between about 10 μs and about 100 μs), and cutting the tissue with the cutting electrode during application of the pulse waveform.

Also described herein are methods for thermo-electrical cutting of biological tissue including the steps of applying a low duty-cycle pulse waveform to a cutting electrode wherein the cutting electrode has peak temperature during application of the pulse waveform of greater than 100° C. and an average temperature during application of the pulse waveform of less than about 50° C. The tissue may then be cut with the cutting electrode during application of the low duty-cycle pulse waveform. In some variations, the average temperature during application of the pulse waveform is less than about 40° C.

Also described herein are methods of simultaneously cutting and hematostais of a biological tissue. Thus, the tissue may be cut in a low duty-cycle pulse waveform that also results in constriction of the vessels adjacent to the cut and thereby decreases the blood flow from the cut tissue. The method may therefore include the steps of contacting a biological tissue with a cutting electrode, applying a low duty-cycle pulse waveform to the cutting electrode (wherein the cutting electrode has an average temperature during application of the pulse waveform of less than about 50° C.), and cutting the tissue with the cutting electrode during application of the low duty-cycle pulse waveform while at least partially constricting the blood vessels adjacent to the cut tissue by application of the low duty-cycle pulse waveform to the cutting electrode.

As described above, the low duty-cycle cutting waveform may involve applying a plurality of pulses having a duty cycle of less than about 10%, less than about 5%, or less than about 2.5%. The low duty-cycle cutting waveform may be a pulse waveform having a plurality of pulses wherein each pulse is made up of a burst of minipulses. The burst of minipulses may be bipolar minipulses. In some variations, the duration of each minipulse within the burst of minipulses is between about 10 ns and about 100 μs. In some variations, the minipulses within each burst of minipulses are continuously applied, while in other variations, there is a delay between minipulses within the burst. In some variations, the low duty-cycle cutting waveform consists of a plurality of bursts of minipulses having an interburst repetition rate of between about 10 Hz and 500 Hz, and a minipulse burst duration of between about 5 μs and about 200 μs. In some variations, the voltage of the pulses within the low duty-cycle cutting waveform may be between about −500 V and about +500 V. Also, the average temperature during application of the low-duty pulse waveform may be less than about 40° C. In some variations, the cutting electrode has a peak temperature during application of the low-duty pulse waveform of greater than about 100° C.

BRIEF DESCRIPTION OF THE DRAWINGS

FIG. 16A FIG. 16A is a graph comparing bleeding using different cutting paradigms, as described herein.

FIG. 16B is a graph illustrating wound strength for cuts made by different cutting paradigms, as described herein.

DETAILED DESCRIPTION OF THE INVENTION

Figure 1:
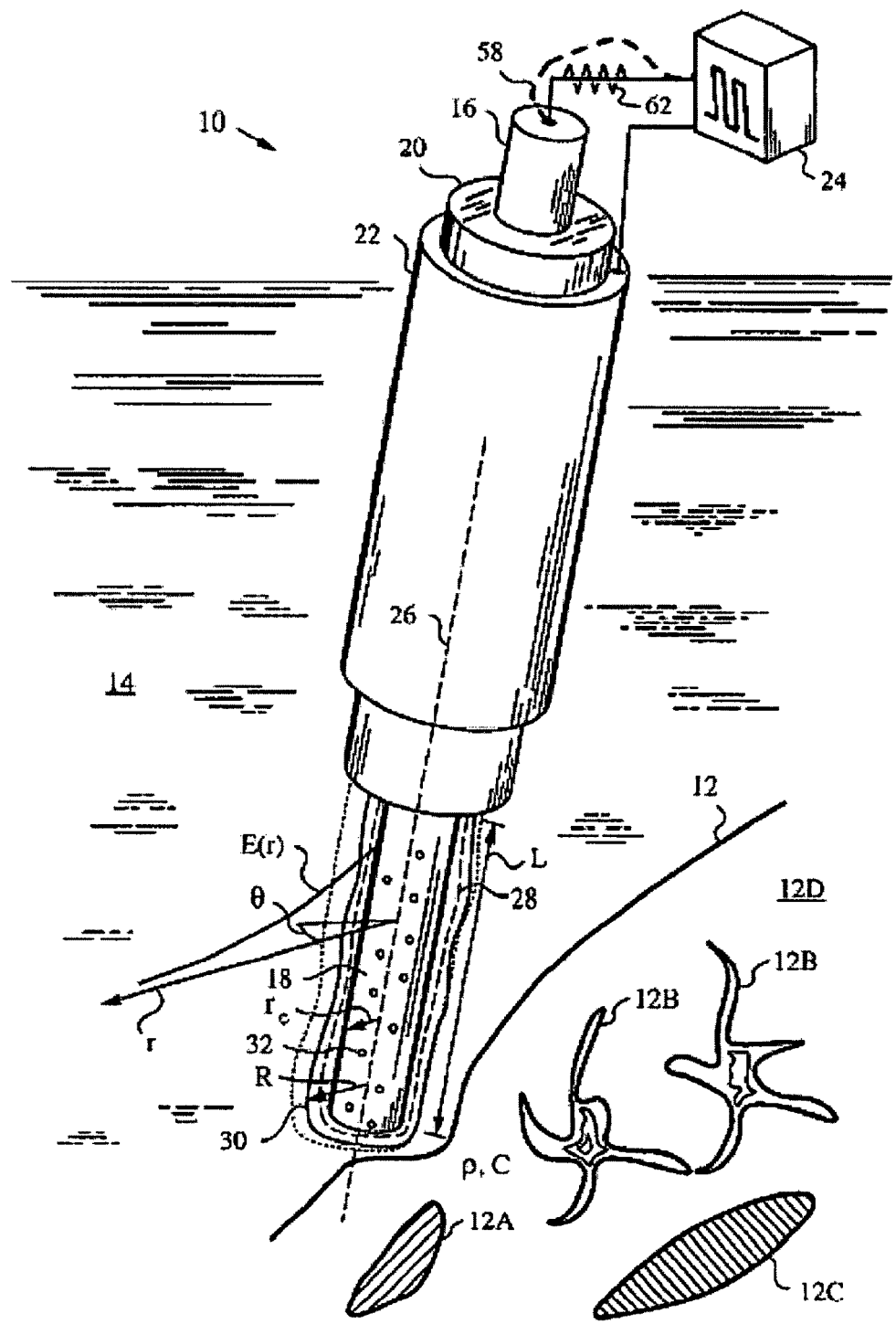
FIG. 1 shows a three-dimensional view of an apparatus according to the invention employed in cutting biological tissue.

FIG. 1 illustrates an apparatus 10 for cutting a material 12 submerged in a conducting liquid medium 14. In this embodiment material 12 is a biological tissue made up of various types of tissue including muscle tissue 12A, nerve tissue 12B, bone 12C and soft tissue 12D. In general, however, material 12 can be any conducting or non-conducting material which requires cutting and can include materials such as cellulose, e.g., wood and cellulose-based materials as well as various types of non-conducting plastics. Liquid medium 14 can be any type of electrolyte. In the present example, liquid medium 14 is a physiological medium, for example an isotonic saline solution.

Apparatus 10 has a cutting electrode 16 with an elongate cutting portion 18. In this embodiment, the entire cutting electrode 16 is in the form of a wire electrode with circular cross section defined by a radius $r_e$. The material of wire electrode 16 can be any suitable conductor such as a metal like Tungsten, Titanium, Molybdenum, etc. or an alloy. In the present embodiment electrode 16 is made of Tungsten wire. Cutting electrode 16 is surrounded by an insulating layer 20 and a return electrode 22. Insulating layer 20 can be any dielectric material or combination of materials such as ceramic, plastic, glass, and/or air that provide electrical insulation between electrodes 16 and 22. Electrodes 16 and 22 are arranged coaxially along a center line 26. Cutting portion 18 protrudes beyond insulating layer 20 and return electrode 22. In fact, a length L of elongate cutting portion 18 is exposed. The aspect ratio of length L to width w ($w=2r_e$) of cutting portion 18 is at least 1 and preferably more than 5.

A voltage control unit 24 is connected to cutting electrode 16 and to return electrode 22. Voltage control unit 24 has a voltage generator for producing a voltage to be applied between electrodes 16, 22. Unit 24 also has a pulse control for pulsing the voltage in accordance with a predetermined modulation format (pulse regime or pulse waveform), as described below. The pulse control has a peak power control and a duration control for adjusting a pulse power, a pulse duration τ and a pulse interval.

The application of a pulse waveform to the cutting electrode may result in the formation of a thin layer of a plasma 28 around elongate cutting portion 18. To achieve this, electrodes 16, 22 of apparatus 10 may be immersed in conductive medium 14 where tissue 12 is submerged and a voltage is applied between electrodes 16, 22 such that medium 14 is heated to produce a vapor cavity 30 around cutting portion 18. During heating, an amount of medium 14 is vaporized to produce a gas 32 inside vapor cavity 30. In the present case medium 14 is saline and thus gas 32 is composed predominantly of water vapor, a small amount of oxygen and hydrogen and trace amounts of NaCl. The layer of gas 32 is ionized in the strong electric field around cutting electrode 16 to make up the thin layer of plasma 28. Because plasma 28 is electrically conductive, it maintains electrical conductivity between electrodes 16, 22. Although many of the examples described herein include the use of a conductive medium, it is to be understood that many of the devices, systems and methods described herein may be used even in the absence of a conductive medium.

As described herein, a cutting electrode may be any electrode with a relatively narrow exposed region so that the vapor cavity and ionization can efficiently occur around the edge. For example, the cutting electrode may have an exposed region that is less than 50 μm thick (e.g., from the edge of an insulation region) and a length, L (where L can be any appropriate length, such as X mm). In some variations, the cutting electrode is a wire that is less than 100 μm in diameter. In some variations, the pulse waveform is matched to the cutting electrode. For example, the cutting electrode may have a length, L and an exposed (uninsulated) cross-sectional area through the length that is less than 100 μm, or less than 50 μm, or less than 20 μm, or less than 10 μm. In general, cutting electrodes may have a long and narrow exposed elongated length, although point cutting electrodes (that are not particularly elongated) may also be used.

Figure 2:
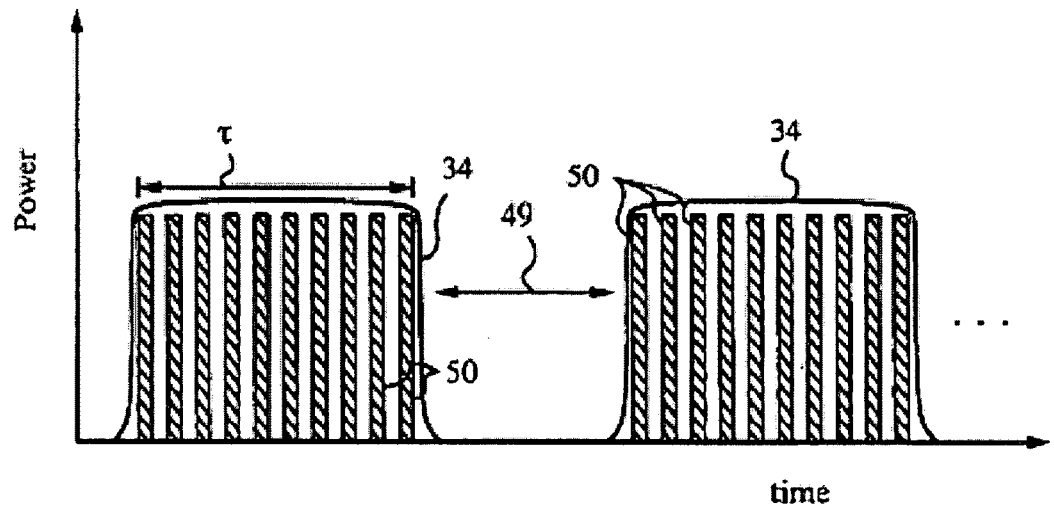
FIG. 2 is a graph illustrating a pulse modulation format according to the invention.

In contrast to the prior art, it is important that the size and rate of formation of vapor cavity 30 as well as heat diffusion into tissue 12 be minimized. The size and rate of formation of cavity 30 are related and can be minimized by modulating the voltage applied between electrodes 16, 22 by the pulse control of unit 24 in accordance with a modulation format, which may also be referred to as pulse waveform. Specifically, a pulse control may modulate the applied voltage in pulses 34, as shown in FIG. 2. The modulation format of pulses 34 is selected to minimize the size of vapor cavity 30, the rate of formation of vapor cavity 30 and also heat diffusion into tissue 12.

Figure 3:
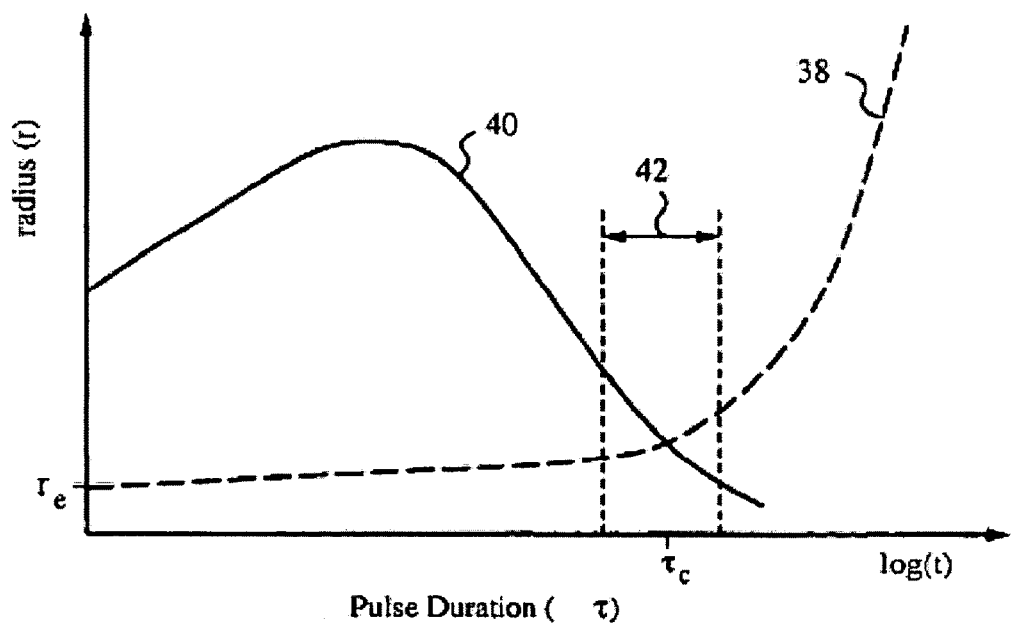
FIG. 3 is a graph indicating the qualitative dependence of the cavitation bubble diameter and heat diffusion on duration of the pulse.

To better understand the principles behind selecting the modulation format to achieve this minimization we now refer to the qualitative graphs in FIG. 3. Graph 38 illustrates the radius around elongate cutting portion 18 to which heat diffuses as a function of duration τ of pulse 34. As duration τ of pulse 34 increases heat diffuses deeper into tissue 12. This diffusion of heat causes thermal damage to tissue 12 and it is to be avoided. It should be noted, that the application of a long train of very high frequency pulses, e.g., RF pulses, will effectively act as one long pulse whose duration is equal to the entire duration of the pulse train. Hence, prior art devices operating in the continuous waveform and applying RF pulses (see Background section) suffer from high heat diffusion and consequently cause large thermal damage to surrounding tissue.

Graph 40 illustrates the maximal radius of vapor cavity in this case also referred to as bubble 30 (see FIG. 1), or cavitation bubble, which is formed at constant pulse energy around cutting electrode 16. Now, the radius of cavitation bubble 30 initially increases with increasing pulse duration τ and then decreases and approaches zero as duration τ of pulse 34 tends to infinity (continuous current). Graphs 38 and 40 intersect at a pulse duration $\tau_c$ at which heat diffusion is still relatively insignificant while the radius of bubble 30 is already small enough not to cause significant tissue damage. Thus, by choosing duration τ of pulse 34 in a range 42 around $\tau_c$ heat damage and mechanical damage due to cavitation bubble 30 are minimized. In fact, choosing duration τ of pulses 34 so as not to produce large cavitation bubble 30 is equivalent to minimizing the size and rate of formation of vapor cavity 30. A person skilled in the art will appreciate that the exact shape of graphs 38, 40 and range 42 will vary depending on specific parameters such the exact composition of tissue 12, salinity of electrolyte 14 and geometry of electrode 16.

Figure 4A:
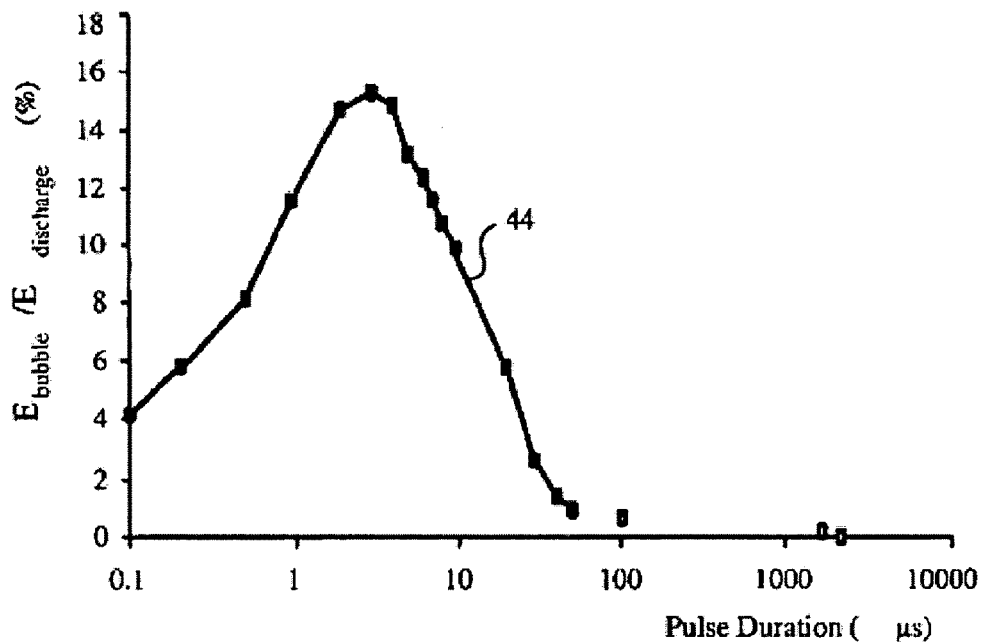
FIG. 4A is a graph illustrating the conversion of electrical energy of the discharge (1 mJ) into the mechanical energy of the bubble measured as a function of pulse duration for the apparatus of FIG. 1.
Figure 4B:
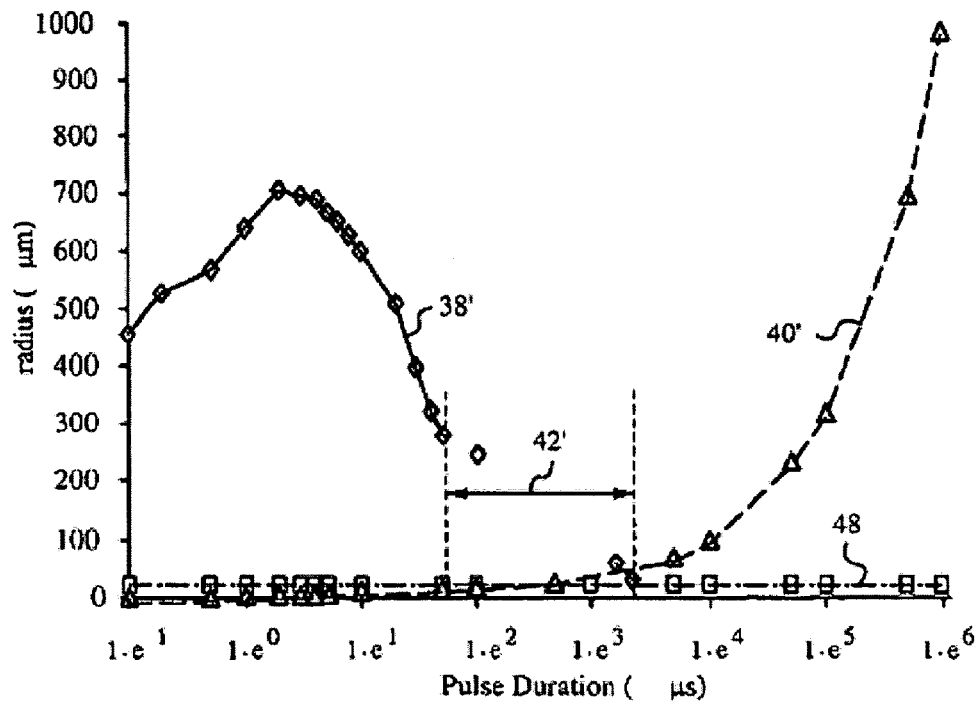
FIG. 4B is a graph illustrating the cavitation bubble size, energy deposition and heat diffusion as a function of pulse duration for the apparatus of FIG. 1.

FIG. 4A shows a graph 44 of the conversion of the electrical energy of the discharge for a discharge energy equal to 1 mJ and electrode 16 diameter of 25 μm into mechanical energy of bubble 30 measured as a function of duration τ of pulse 34. Efficiency of the conversion decreases with increasing duration τ of pulse 34 once pulse 34 is longer than about 3 μs. In FIG. 4B the radius of single bubble 30 is illustrated by graph 38' as a function of pulse duration τ in a 1 mJ discharge. At pulse duration τ above 50 μs a sequence of bubbles is formed with maximal radii reducing with increasing duration τ, as depicted by separate rhombuses. Graph 48 represents the penetration depth into material 12 of electric field E(r), here equal to radius $r_e$ of cutting portion 18. Graph 40' represents the radius around cutting portion 18 to which heat diffuses assuming constant temperature of cutting portion 18 in one dimensional geometry.

A range 42' in which pulse duration τ is optimized and in which both cavitation and heat diffusion are comparable with field penetration depth is between 50 µs and 2 ms. Under different conditions range 42' will vary, but optimal duration τ of pulses 34 will generally fall between 10 µs and 10 ms. In this range 42' the size and rate of formation of vapor cavity 30 as well as heat diffusion into tissue 12 are minimized. The thermal damage zone in tissue 12 due to heat diffusion is dependent mostly on duration τ of pulse 34. Specifically, varying duration τ of pulses 34 between 0.1 and 100 ms changes the depth of the heated zone in tissue 12 between 10 and 300 µm ranging from single cellular layer with no hemostatic effect to complete hemostasis in most of tissues 12A, 12B, 12C and 12D.

In the exemplary pulse waveform shown in FIG. 2, pulses 34 can be delivered in various modulation formats including continuous pulses or bursts of short pulses or minipulses 50. Thus, a pulse may be a burst of minipulses having a duration for the burst of minipulses equal to τ. Pulses 34 may be separated by a separation 49 of at least 1 ms, and preferably at least 2 ms while pulses 34 themselves are composed of a number of minipulses 50, as shown. The amplitude and duration of minipulses 50 determine the spatial extent and density of plasma 28. To avoid excessive overheating of tissue 12 the modulation format is adjusted so that plasma 28 is maintained at the regime of streamer and spark discharges but the arc discharges are prevented. Specifically, duration and peak power of minipulses 50 are adjusted to permit spark discharges and to prevent arc discharges. In most cases, limiting the duration of minipulses 50 to less than several µs will accomplish this goal. In fact, the duration of minipulses 50 may be kept in the range between 10 ns and 100 µs and preferably between 0.2 and 5 µs. The interval between minipulses 50 is preferably selected in the range between 0 (e.g., continuous) and 10 µs. Such short times are sufficient for ionization and development of the spark discharges but not for creation of the arc discharge.

An arc discharge is a highly luminous and intensely hot discharge of electricity between two electrodes, in this case between electrode 16, and more precisely its cutting portion 18, and return electrode 22. The arc discharge is initiated when a strong electric forces draw electrons from one electrode to the other, initiating the arc. It is typically a continuous discharge characterized by high current and low voltage across the arc. On the other hand, a spark discharge has a high voltage and short duration.

If the intervals between minipulses 50 do not exceed a lifetime of vapor cavity 30, the ionization will be maintained by minipulses 50 until vapor cavity 30 collapses. Hence, in any situation, the intervals between minipulses 50 should be kept shorter than the lifetime of vapor cavity 30. For example, the lifetime of a 100 µm wide vapor cavity 30 is about 10 µs, thus minipulses 50 should be delivered at intervals not longer than 10 µs when working with such cavity width.

In contrast to prior art devices, apparatus 10 cuts tissue 12 using a side or edge of cutting portion 18, i.e., the entire length L of cutting portion 18 is available for performing the cut. Rapid and efficient ablation of tissue 12 may be achieved when the temperature of cutting portion 18 and layer of plasma 28 around it are maintained significantly above the boiling temperature of water. In some variations, the temperature is efficiently maintained by having the cutting portion 18 be long and thin, i.e., having a small radius—a few tens of microns—and an aspect ratio (length to width) of at least 1 and preferably at least 5. Such thin cutting portions 18 also reduce the amount of heat flow through the metal back into a hand piece (not shown).

In fact, heat flow W through cutting portion 18 in this example is equal to:

$$W = \chi \Delta T S / L$$

where $S = \pi d^2/4$ is the cross section area of cutting portion 18. In the above equation χ is the coefficient of thermal conductivity and ΔT is the difference in temperature between the hot and cold parts of wire electrode 16, L is the length of cutting portion 18 and $d = 2r_e$. Evaporation rate of tissue 12 is equal to:

$$V = L d v$$

where v is the velocity of advance of cutting portion 18 through tissue 12. The amount of power deposited in tissue 12 to achieve such evaporation rate is:

$$P = V \cdot \rho (C \Delta T_1 + \delta)$$

where ρ is the density of tissue 12, C is its heat capacity, $\Delta T_1$ is the temperature rise from ambient to 100° C., and δ is the specific heat of evaporation (for tissue mostly composed of water the specific heat of evaporation of water $\delta = 2.26 \times 10^3$ J/g can be used in the calculation). To prevent cooling of cutting portion 18 and of layer of plasma 28 by heat transfer via electrode 16, power deposition P should be kept significantly larger than the heat flow W, i.e., P>>W. In the present example, electrode 16 is made of Tungsten which has a heat conductivity η=178 W/m*K, $\Delta T_1$=70° K. and cutting portion 18 is advanced through tissue 12. For example, at ΔT=250° K. and v=1 mm/s one obtains the condition $L^2/d$>>14 mm from the above equations. Therefore, to efficiently prevent cooling when cutting portion 18 has a length L=1 mm the diameter $d=2r_e$ of cutting portion 18 should be less than 70 µm. For ΔT=70° K. and the rest of the parameters remaining the same we will obtain the conditions $L^2/d$>>4 mm. This means that a 1 mm long cutting portion 18 should not be thicker than 250 microns.

In some variations, the temperature of cutting portion 18 can be maintained as low as about 100° C., but it may be much higher, ranging up to 1000° C. In this temperature range tissue 12 is rapidly evaporated and thus ablated. Due to the turbulent flow of liquid boiling at the edges of vapor cavity 30 the interface with tissue 12 is only minimally overheated and damaged.

In the regime of heating produced by plasma 28 the temperature of cutting portion 18 may be stabilized by a naturally occurring negative feedback mechanism as follows. In the areas where the vapor sheet of cavity 30 becomes thinner, the electric impedance is reduced and thus more current flows. The increased current results in increased generation of Joule heat in that area, and thus more electrolyte 14 is evaporated thereby increasing the thickness of vapor cavity 30 in that area. This mechanism stabilizes the thickness of vapor cavity 30 around cutting portion 18 and the thermal conditions of cutting portion 18. When tissue 12 is brought into ionized vapor cavity 30, thus reducing its thickness in that area, more current flows into tissue 12 than into plasma 28, since the impedance of tissue (which is typically similar to that of electrolyte 14) is much lower than that of plasma 28. Thus, more heat is generated in the area where tissue 12 is positioned inside vapor cavity 30.

Application of thin elongated electrode (for example a wire electrode) may allow for minimization of the amount of material evaporated during tissue dissection as well as for minimization of the depth of the damage zone produced at the edges of the cut, as shown below. In the present embodiment, the electric field E(r) around cylindrical cutting portion 18 is reciprocal to the distance from it, and the density of Joule heat generated in liquid by the discharge is reciprocal to the square of that distance. Thus, thinner cutting portion 18 results in a more confined energy deposition. In fact, the electric field E(r) around cylindrical cutting portion 18 scales with distance r as follows:

$$E = \frac{(E_e r_e)}{r}$$

where $E_e$ is the value of the electric field on the surface of cutting potion 18. Thus, the difference in voltage on the surface of cutting portion 18 and at a distance R from electrode 16 is:

$$U_e - U_R = \int_R^{r_e} E(r) dr = E_e r_e (\ln R - \ln r_e).$$

The electric field becomes spherical at distances larger than length L of cutting portion 18, and thus it can be assumed that the electric potential drops to zero for distances larger than L. Therefore, the electric field $E_e$ at the surface of cutting portion 18 is:

$$E_e = \frac{U_e}{r_e(\ln L - \ln r_e)}.$$

The power density w of the Joule heat generated in electrolyte 14 is then:

$$w = j^2 \gamma = \frac{E_e^2}{\gamma} = \frac{U_e^2}{r_e^2(\ln L - \ln r_e)^2 \gamma},$$

where j is the current density and γ is the resistivity of electrolyte 14. The minimal energy density for overheating of the surface layer of electrolyte 14 (assumed to be water) by pulse 34 of duration τ is:

$$A = w \cdot \tau = \rho \cdot C \cdot \Delta T$$

where ΔT is the total temperature rise in the surface layer of electrolyte 14 during pulse 34, ρ is the density of water and C is its heat capacity. Therefore, the voltage U required for initiation of vaporization during pulse 34 of duration τ is:

$$U = r_e (\ln L - \ln r_e) \sqrt{\rho \cdot C \cdot \Delta T \cdot \gamma / \tau}.$$

The voltage U and associated energy deposition can be reduced by decreasing the radius $r_e$ of cutting portion 18. In general, ambient temperature is about 30° C. when operating in biological tissue 12 of a live subject, boiling temperature is 100° C., ρ=1 g/cm³, C=4.2 J/(g·K) and γ~70 Ohm·cm. With these values we obtain A~300 J/cm³ and U=260 V for pulse 34 of duration τ=0.1 ms, $r_e$=25 μm and L=1 mm.

Since the electric field is reciprocal to the distance from the cylindrical electrode, the field efficiently penetrates into the electrolyte to the depth similar to the radius of the electrode. This minimal amount of energy required for creation of the vapor cavity around the electrode is:

$$A = w \cdot \tau = \rho \cdot C \cdot \Delta T \cdot \pi \cdot d^2 \cdot L,$$

where d is the diameter of the electrode. Minimal depth of the damage zone at the edges of the cut will thus be similar to the radius of the electrode. Thus, reduction in radius of the electrode results in reduction in the power consumption and in the width of the damage zone produced at the edges of the cut. The threshold voltage $U_{th}$ required for reaching the threshold electric field $E_{th}$ to ionize gas 32 and produce plasma 28 is:

$$U_{th} = E_{th} r_e \ln(R/r_e),$$

where R is the radius of vapor cavity 30, as shown in FIG. 1. Threshold voltage $U_{th}$ can be decreased by reducing radius $r_e$ of cutting portion 18. This also results in a lower power dissipation and consequently in a smaller damage zone in tissue 12.

Vapor cavity 30 filled with plasma 28 and surrounding cutting portion 18 of cutting electrode 16 serves three major functions. First, it thermally isolates cutting electrode 16 from electrolyte 14 thus allowing for efficient heating. Second, the electric impedance of plasma 28 is much higher than that of tissue 12, thus Joule heating is generated mostly in plasma 28 and not in the surrounding liquid environment. Third, since both electrical and thermal conductivity of tissue 12 is much higher than that of a vapor (gas 32), when tissue 12 is introduced inside vapor cavity 30 with plasma 28 it attracts both electric current and heat flow, which results in fast overheating and evaporation.

Another advantage of the cylindrical geometry of cutting electrode 16 as compared to prior art point sources (inlaid disc geometry) is that it allows for cutting tissue 12 with the side edge of cutting portion 18. Prior art point sources (see U.S. Pat. No. 6,135,998) produce a series of perforations when a train of pulses is applied. These perforations do not always form a continuous cut leaving behind bridges between the edges of the cut. To dissect these bridges the secondary scans are required and targeting these thin and often transparent straps of tissue is very difficult and time consuming. Cylindrical cutting portion 18 solves this problem by enabling the cutting by its edge and not only by its end or tip.

Figure 5:
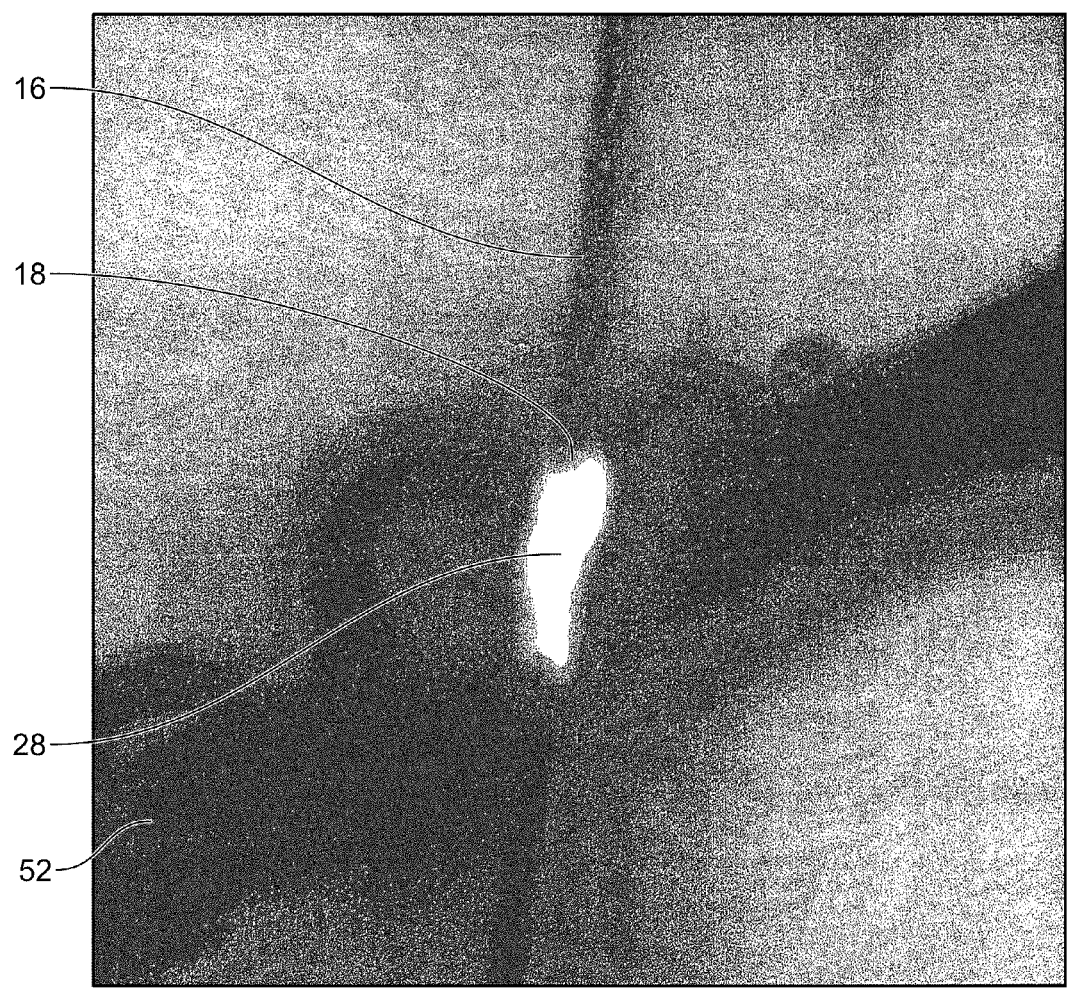
FIG. 5 is a photograph of the use of cutting electrode with elongate cutting portion for cutting paper.

In order to reduce unnecessary energy deposition, e.g., during electrosurgery, the voltage of source 24 can be set to a level which is sufficient for ionization of only a thin layer of vapor. Thus, in areas where vapor cavity 30 is too large (typically above several tens of microns) no plasma 28 will be formed. As a result, ionization and formation of plasma 28 will only take place in the areas of proximity or contact between generally conductive tissue 12 and conductive cutting portion 18. In other parts of vapor cavity 30 gas 32 will not be ionized and thus it will electrically insulate cutting electrode 18 preventing heat deposition into the surrounding environment. FIG. 5 illustrates cutting electrode 16 with cutting portion 18 of radius $r_e$=25 μm immersed in isotonic saline solution touching the edge of a material 52. This figure shows clearly the formation of plasma 28 at the point of contact with material 52. In this case material 52 is made of cellulose and is in fact a sheet of paper. Cutting portion 18 is touching an edge of material 52 that is about 250 μm thick. As is clearly seen, plasma 28 is generated only in the area of contact between cutting electrode 18 and paper 52.

Although the cutting electrodes described above (including the derived equations) are predominantly wire electrodes, other cutting electrodes may be used. In particular, blade or knife-type cutting electrodes may be used, in which only the cutting edge (e.g., an exposed edge region is uninsulated).

Figure 6:
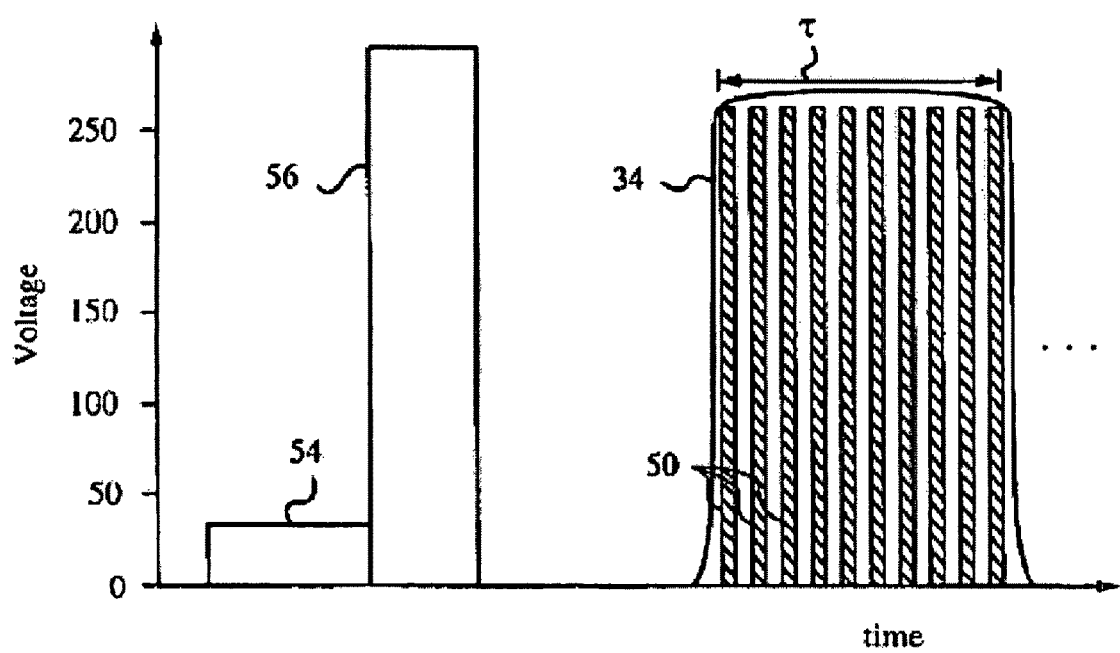
FIG. 6 is a graph of a pre-pulse and post-pulse used in accordance with the invention.

To further reduce the energy deposition, cavity 30 can be created by electrochemical generation of gas 32, i.e., by electrolysis of water, rather than by its vaporization. For this purpose the pulse control and source 24 can vary the voltage between parts of the pulse or even between two successive pulses, as shown in FIG. 6. First, source 24 applies a pre-pulse 54 of relatively low voltage. This low voltage should be sufficient for electrolysis and can be in the range of several tens of Volts. In accordance with well-known principles, the application of such low voltage will yield oxygen gas on the anode and hydrogen gas on the cathode. The user can choose whether to use oxygen or hydrogen as gas 32 by selecting the polarity of pre-pulse 54, such that cutting portion 18 is either the anode or cathode. It should be noted, that applying a pulse composed of minipulses with alternating polarity (see FIG. 8 and below description) will generate a mixture of oxygen and hydrogen.

Next, pulse control and source 24 increases the voltage to a relatively high level in a post-pulse 56. The voltage of post pulse 56 can be in the range of several hundred Volts to complete the formation of vapor cavity 30 and to ionize gas 32 to form plasma 28. A sequence of combination pulses containing pre-pulse 54 and post-pulse 56 can be used to drive apparatus 10. Alternatively, a single combination pulse can be followed by a series of regular pulses 34 composed of minipulses 50, as described above. Embodiments of the method taking advantage of electrochemical generation of gas 32 around cutting portion 18 of electrode 16 obtain a substantial pulse energy reduction.

The rate of evaporation of electrolyte 14 may depend on its temperature. There is always a delay between the moment when electrolyte 14 reaches boiling temperature (boiling temperature of water) and the moment when formation of vapor cavity 30 disconnects the current flowing through electrolyte 14 between electrodes 16, 22. When vapor cavity 30 forms, gas 32 stops the current flow and prevents further heating. Just before this time an additional energy is deposited that leads to overheating of electrolyte 14 and thus to explosive (accelerated) vaporization. This effect results in formation of a larger vapor cavity 30 and turbulence around cutting portion 18 of electrode 16. To prevent such overheating the energy for initial boiling should be delivered at a lower voltage, but as soon as vapor cavity 30 is formed, the voltage should be increased to achieve fast ionization of gas 32. Several solutions can be employed to address this problem.

In accordance with a first solution, a low impedance line 58, as indicated in dashed line in FIG. 1, is used instead of a standard electrical connection between the output of pulse generator in unit 24 and cutting electrode 16. In accordance to well-known principles, low impedance line 58 will cause the rising edge of a pulse to be reflected from the output end if the output impedance is high. This condition occurs when vapor cavity 30 is formed and not while electrode 16 is in direct contact with electrolyte 14. The reflection will oscillate within line 58 with a period determined by its length, and will form a high frequency (several MHz) modulation.

Figure 7:
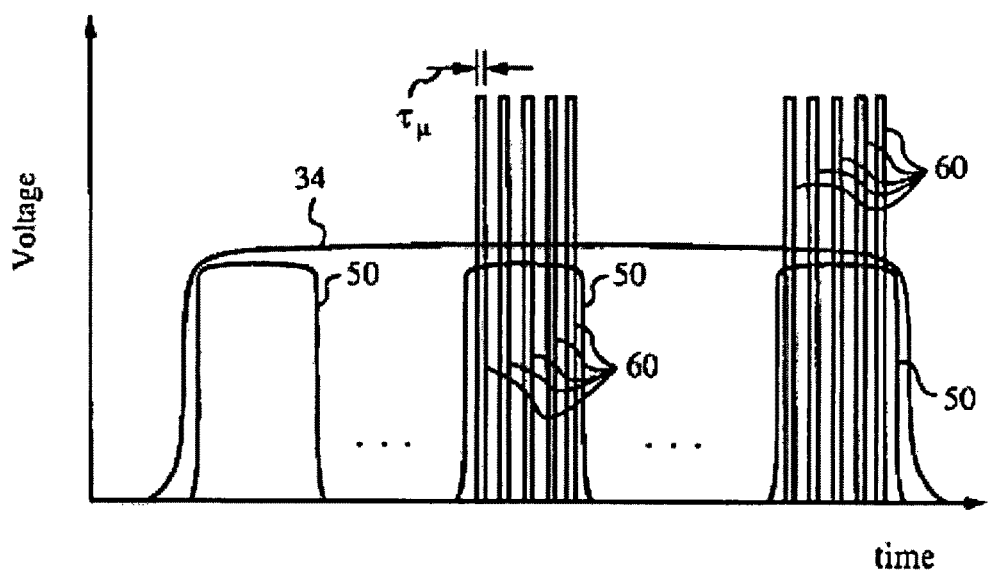
FIG. 7 is a graph illustrating the use of micropulses in accordance with the invention.

FIG. 7 illustrates the effect of line 58 on minipulses 50 in a pulse 34. The first set of minipulses 50 does not experience any changes because at this time the output impedance is still low (vapor cavity 30 not yet formed). Once vapor cavity 30 is formed reflection occurs and micropulses 60 are generated. As a result, each minipulse 50 gives rise to a series of micropulses 60. The length of line 58 is selected such that micropulses 60 have a duration $\tau_\mu$ in the range between 0.1 and 1 µs. The voltage of micropulses 60 is twice as high as that of minipulse 50. This doubling in voltage of micropulses 60 is beneficial because it aids in ionizing gas 32 to form plasma 28 more rapidly and depositing more energy in plasma 28 than it was possible with minipulse 50 at the lower constant voltage level. That is because energy deposition increases as the square of the voltage and only linearly with the amount of time the voltage is applied. Hence, although micropulses 60 are applied at electrode 16 only about half the time of a minipulse 50, their doubled voltage raises the energy deposition by a factor of four.

In accordance with another solution an increase in the rate of ionization of gas 32 is achieved by adding a ballast resistor 62 in series with the load, as shown in dashed lines in FIG. 1. The resistance of resistor 62 ($R_{ballast}$) is selected to be higher than the impedance of the discharge in electrolyte 14 ($R_{electrolyte}$) but lower than in the ionized vapor or gas 32. As a result, the heating of electrolyte 14 before evaporation will proceed at a lower voltage $U_{low}$:

$$U_{low}=U(1+R_{ballast}/R_{electrolyte}).$$

The reduced voltage will slow the boiling and cause formation of thinner vapor cavity 30. After evaporation the impedance will greatly increase, resulting in an increase of the discharge voltage to a high value $U_{high}$:

$$U_{high}=U(1+R_{blast}/R_{vapor}).$$

At this high voltage ionization of gas 32 will proceed rapidly. Specifically, when cutting portion 18 has a diameter of 50 µm and its length L=1 mm the impedance of the discharge in saline 14 is about 500 Ohms, while in plasma 28 it is about 6 KOhms. Thus, for example, a ballast resistor of 1 kOhms will provide output voltages of $U_{low}$=U/3 and $U_{high}$=U/1.17, respectively. The lower limit to the voltage applied during the heating phase is set by how much the duration of minipulses 50 and pulses 34 can be increased without unacceptable thermal damage to tissue 12 is caused by increased heat diffusion.

Figure 8:
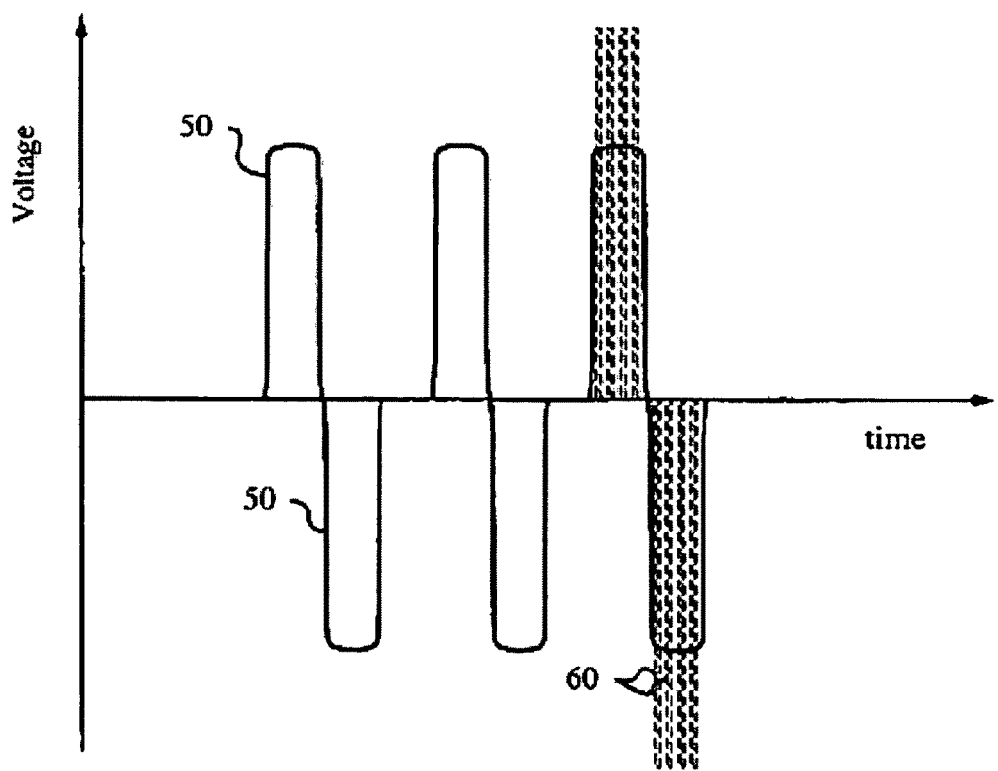
FIG. 8 is a graph illustrating the use of minipulses of alternating polarity in accordance with the invention.

In yet another embodiment the method of invention is adapted specifically for cutting biological tissue 12 containing muscle tissue 12A and nerve tissue 12B. It is known that electric excitation of nerve tissue 12B leads to contractions in muscle tissue 12A. In order to avoid contraction of muscle tissue 12A and reduce the risk of electroporation of adjacent tissue the method of invention calls for limiting and preferably stopping any charge transfer to tissue 12. This may be achieved by using minipulses 50 of alternating positive and negative polarities, as illustrated in FIG. 8. Low impedance line 58 can also be used to generate micropulses 60 when vapor cavity 30 is formed.

The polarities may be set by the voltage source of unit 24 in accordance with well-known electronics techniques. In the present embodiment the alternating polarities can be produced by a separating capacitor (not shown). The discharge time constant of the RC circuit, where R is the resistance of the discharge, should not exceed the excitation time of nerve cells in nerve tissue 12B at the applied voltage level. A person skilled in the art will appreciate that exact RC time constant will have to be adjusted on a case-by-case basis. In general, however, contractions of muscle tissue 12A will be prevented at a voltage level of 500 Volts if the discharge time does not exceed 1 µs. When cutting portion 18 has a diameter of 50 µm and length L=1 mm the electrical impedance is about 500 Ohms, and hence the capacitance of capacitor should not exceed 2 nF. It should be noted that in addition to preventing muscular contractions, alternating polarity of minipulses 50 reduces the effect of electroporation, as compared to direct current (DC) (only positive or only negative voltage) pulses.

Figure 9:
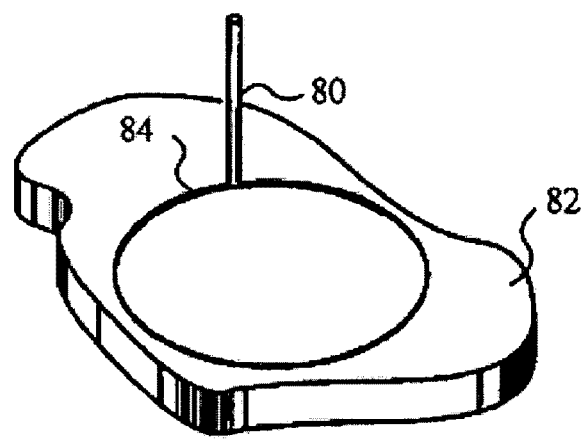
FIG. 9 illustrates an apparatus of the invention used in cutting a material.

Various alternatives can be introduced to the apparatus of invention depending on the material being cut and the type of cut required. For example, in FIG. 9 a cutting electrode 80 of an apparatus analogous to apparatus 10 is used for performing a circular incision 84 in a material 82. The return electrode and liquid conducting medium are not shown in this drawing. Material 82 is a thin sheet of plastic or biological material. When used for performing biopsy, a cylindrical biopsy can be easily obtained in this manner without bleeding.

Figure 10:
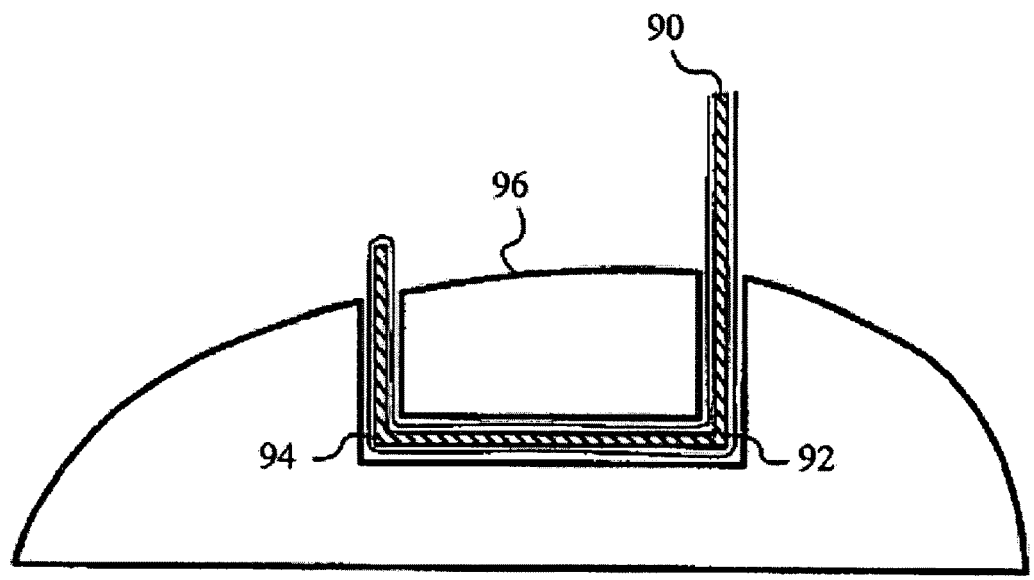
FIG. 10 illustrates an apparatus of the invention using a shaped cutting electrode.

FIG. 10 illustrates a cutting electrode 90 having two bends 92, 94 to form a U-shaped electrode. The return electrode and liquid conducting medium are not shown in this drawing. Cutting electrode 90 is used for removing a large amount of a material 96 with a single cut. U-shaped cutting electrode 90 can be used to minimize the damage to tissue in electrosurgery and to maximize the lifetime of cutting electrode 90. In an alternative version a cutting electrode with a single bend can be used to make and L-shaped cutting electrode. In general, bends at various angles can be introduced to cutting electrode to perform any desired type of cut, to approach tissue at various angles and to manipulate the tissue before and during the cutting.

Figures 11A, 11B, 11C:
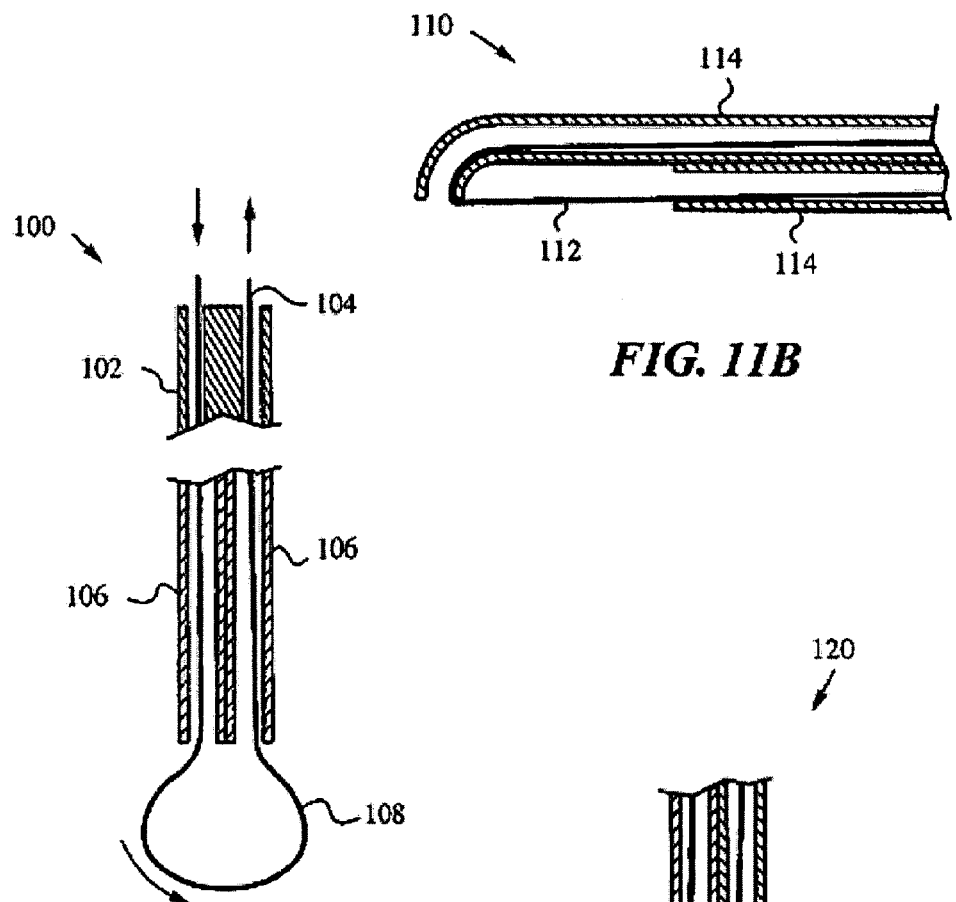
FIGS. 11A-C are partial views of alternative embodiments in accordance with the invention.

FIG. 11A illustrates a portion of yet another apparatus 100 having a mechanism 102 for advancing a cutting electrode 104. In this embodiment cutting electrode 104 is a wire electrode. Return electrode 106 is in the form of two capillaries through which wire electrode 104 is threaded. Capillaries 106 can be used for delivering an electrolyte and/or aspirating fluids during electrosurgery, i.e., capillaries 106 can be used for irrigation and suction. Cutting electrode 104 forms a loop 108 for cutting tissue in accordance with the method of the invention. Mechanism 102 allows the user to refresh cutting electrode as needed during operation. Exposure time of wire electrode 104 outside capillaries 106 should be smaller than its erosion lifetime. It should be noted that mechanism 102 can be used in other embodiments for both advancing and retracting the cutting electrode as necessary to maximize its lifetime and/or retract an eroded electrode.

FIG. 11B illustrates a portion of an apparatus 110 using a wire electrode 112 threaded through capillaries 114. Capillaries 114 serve the dual function of return electrode and channels for delivering and aspirating fluids during operation. Apparatus 110 can be used as a frame saw, as required in electrosurgical applications. FIG. 11C illustrates a portion of still another apparatus 120 functioning as a stationary scissors for both lifting and cutting of tissue. Apparatus 120 has a cutting electrode 122 in the form of a wire threaded through two capillaries 124 functioning as the return electrode. Mechanism 102 allows the user to refresh cutting electrode as needed during operation. Exposure time of wire electrode 112 outside capillaries 114 should be smaller than its erosion lifetime. A projection 126 is used for lifting of tissue. Both apparatus 110 and apparatus 120 are operated in accordance with the method of the invention.

Figure 12:
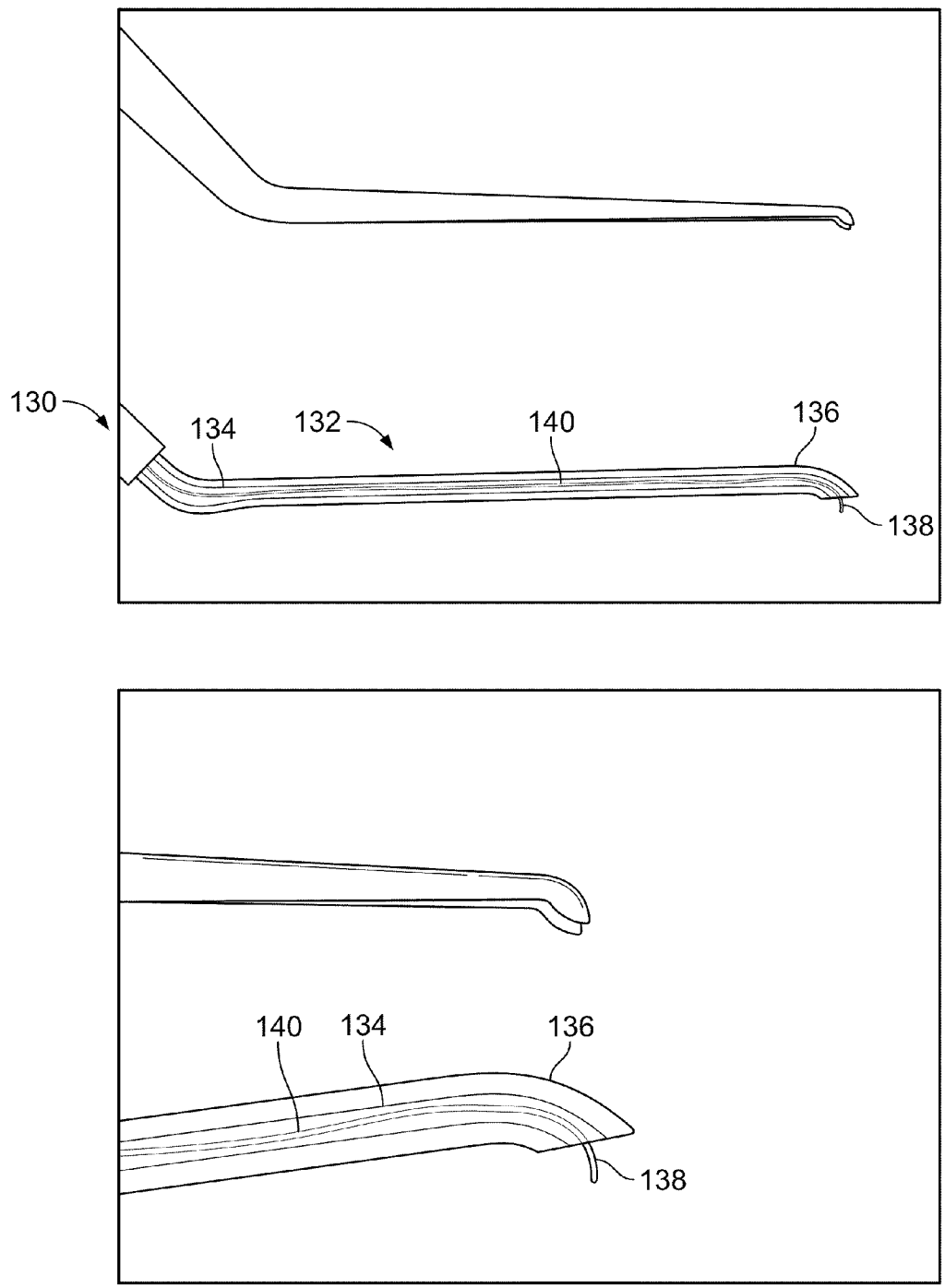
FIG. 12 illustrates an apparatus of the invention designed for capsulotomy.

FIG. 12 illustrates a portion of an apparatus 130 specifically designed for capsulotomy. An electrosurgical probe 132 for capsulotomy has a shape similar to the mechanical tools used for capsulotomy in order to make its application easy and convenient for surgeons who are used to such mechanical tools (comparison is shown in the top photograph). Probe 132 has an insulator 134 with external diameter varying between 0.1 and 1 mm, which has a bent tip 136 at the end. A cutting electrode 138 with a diameter varying between 10 to 200 microns protrudes from insulator 134 by a distance varying between 20 microns to 1 mm. A return electrode 140 can be either a concentric needle or an external electrode attached to the eye or somewhere else to the body of the patient. Apparatus 130 protects the tissue located above the lens capsule (cornea and iris) (not shown) from accidental contact with cutting electrode 138 thus ensuring its safe use during capsulotomy.

Duty Cycle

The pulse waveforms described herein operate at a low duty cycle, typically less than or equal to 0.1 or 10%. In some variations, the low duty-cycle pulse waveform for cutting includes repeated bursts of minipulses, where each burst of minipulses is separated by an interburst (or interpulse) interval. Each burst of minipulses allows a complete cycle of action of the cutting electrode. Thus, each burst of minipulses may perform a complete cycle of vaporization, ionization, and termination, necessary for cutting by the electrode, as described above.

Duty cycle is generally understood as the ratio of "on" time to "off" time for an electronic component or signal. This ratio (which may range from 0 to 1), may also be expressed as a percent (from 0% to 100%). In a pulsed waveform (e.g., the pulse regime), the duty cycle may be defined as the ratio of (a) the sum of all pulse durations during a specified period of continuous operation to (b) the total specified period of operation. The methods and devices described herein describe plasma-mediated thermo-electric ablation having a low (e.g., less than 10%, less than 5%, less than 2%, less than 1% and less than 0.1%) duty cycle during cutting using the cutting pulse waveform. In operation, this low duty cycle may result in substantially lower damage to adjacent tissues, since the total energy applied to the tissue is much lower than higher duty-cycle methods, and is applied in a much more precise manner than other electrosurgical techniques. As described in more detail below, the lower energy applied may be seen when observing the heat of the cutting electrode during cutting.

Figure 13A:
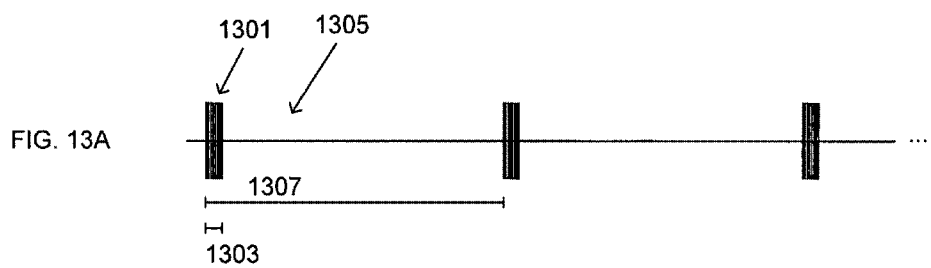
FIGS. 13A-13E illustrate various low duty-cycle pulse regimes (waveforms).

In addition to the low duty-cycle pulse waveforms previously described, FIGS. 13A-13E illustrate additional low duty-cycle pulse waveforms that may be used to cut tissue as described herein. The general pulse waveform shown in FIG. 13A is similar to the pulse waveform shown and described above in FIG. 2. In FIG. 13A, the pulse waveform consists of repeated bursts 1301 of minipulses. As mentioned above, a burst of minipulses may also be referred to as a pulse or a burst. Each burst of minipulses has a minipulse duration 1303, and is separated from the next burst of minipulses by an interburst interval 1305. Thus, the bursts of minipulses are repeated at a repetition rate ("rep rate"). Table 1, below, illustrates examples of values for the rep rate, and minipulse burst duration for various low duty-cycle pulse waveforms. For example, a pulse waveform for a low-duty cycle of less than about 10% duty cycle may have a rep rate of between about 10 Hz and 1 KHz (e.g., an interburst interval of approximately 1 ms to 100 ms), and a minipulse burst duration (pulse duration) of between about 10 μs and 100 μs. In some variations, a pulse waveform for a low-duty cycle of less than 10% duty cycle may have a rep rate of between about 10 Hz and 500 Hz and a minipulse burst duration of between about 5 μs and about 200 μs or between about 10 μs and 200 μs. An exemplary pulse waveform for a low-duty cycle of less than about 5% duty cycle may have a rep rate of between about 10 Hz and 500 Hz (e.g., an interburst interval of approximately 2 ms to 100 ms), and a minipulse burst duration (pulse duration) of between about 10 μs and 100 μs. An exemplary pulse waveform for a low-duty cycle of less than about 2.5% duty cycle may have a rep rate of between about 10 Hz and 250 Hz (e.g., an interburst interval of approximately 1 ms to 100 ms), and a minipulse burst duration (pulse duration) of between about 10 μs and 100 μs.

Figure 13B:
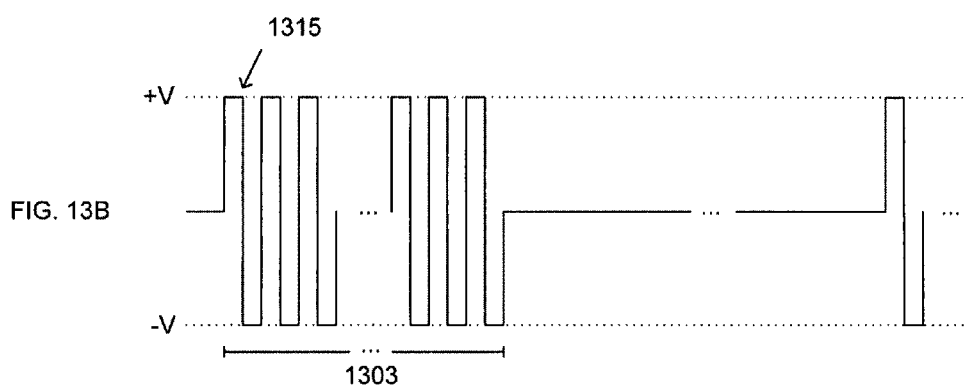
Figure 13C:

FIG. 13B shows a magnified view of the burst of minipulses 1301 within a low duty-cycle pulse waveform. The burst of minipulses includes a plurality of minipulses 1315. In FIG. 13B, the minipulses are each identically shaped. As previously described, the minipulses may have different pulse shapes. Each of the minipulses shown in FIG. 13B are bipolar minipulses, so that each minipulses have a positive and a negative voltage component (+V and −V). In some variations, the minipulses are not bipolar, but are monopolar, or have alternating polarities. FIG. 13C illustrates a burst of pulses 1316 that are not bipolar. The minipulses in FIG. 13B are also not separated by an intraburst interval (e.g., the time between minipulses is 0 s). Thus, the burst of minipulses in FIG. 13B is a continuous burst of minipulses, within the burst. In some variations, there is an intraburst interval that is non-zero. Fore example, the intraburst interval may be between 10 ns and 50 µs.

The duration of each minipulse within the burst of minipulses may be selected from an appropriate range, as previously described. For example, in some variations, the duration of the minipulse is between about 10 ns and about 10 µs. Table 1 also gives some exemplary values of minipulse duration, duration between minipulses (intraburst interval) and the number of minipulses. The minipulses within each minipulse burst may have any appropriate voltage, as described above, particularly for the initiation and maintenance of plasma. For example, the voltage may be between about ±600 V, or between about ±500 V, or between about ±400 V.

Figure 13D:
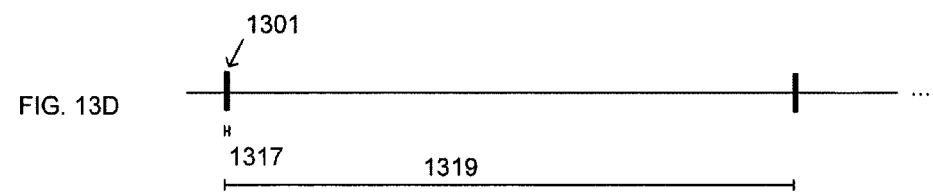
Figure 13E:
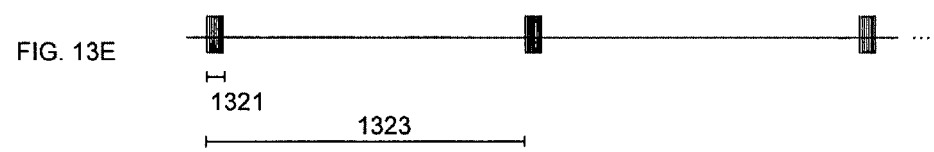

FIG. 13D shows an example of a pulse waveform having a duty cycle of less than 1% (e.g., 0.01%). In this example, the minipulse burst duration 1317 is approximately 10 µs, and the rep rate 1319 is approximately 10 Hz. The minipulses within the burst are bipolar, and are continuous. FIG. 13E is another example of a low duty-cycle pulse waveform. In this example, the duty cycle is approximately 5%. The burst duration 1321 is approximately 100 µs, and the rep rate is approximately 500 Hz. Other exemplary pulse waveform parameters are shown in Table 1.

adjusted to affect efficient cutting. For example, the duty cycle or relevant parameters may be selected from within a preset range, or from within a table of preset values.

In some variations, the pulse generator and/or voltage control unit allows selection and control of the pulse waveform applied. The pulse waveform applied may be matched to information provided to the system. For example, the cutting electrode may communicate with the voltage control unit or pulse generator (generally referred to as the power supply), indicating that the exposed portion of the cutting electrode has a particular length and/or width, and/or shape. The pulse waveform applied may be selected, in part, based on this information.

The voltage control unit and/or power supply may also include user input to select the low-duty cycle pulse waveform. In some variations, the voltage control unit may include control circuitry for calculating or determining duty-cycle, either directly or by approximation. In some variations, the voltage control unit may have a regulator or governor that prevents the duty-cycle for a cutting pulse waveform to exceed 10%, 5%, 2.5%, etc. Thus, only low duty-cycle pulse waveforms may be applied for cutting. The pulse waveform may be selected by allowing selection of some or any of the parameters described. For example, the duty-cycle for cutting may be selected directly. In some variations, the pulse duration is selectable. The rep rate of the burst of minipulses is selectable (within a range, e.g., 10 Hz-500 Hz). In some variations, the duration of the burst of minipulses is selectable within a range, e.g., 10 µs-100 µs). In some variations, the duration of the minipulses is selectable within a range, e.g., 10

TABLE 1

Exemplary Low duty-cycle pulse waveform parameters

| Duty Cycle | Minipulse Burst Repetition rate | Minipulse burst duration | Minipulse Duration | Number of Minipulses | Interval Between Minipulses |
|---|---|---|---|---|---|
| ~10% | 1 KHz | 100 µs | 10 ns | 5000 | 10 ns |
| ~5% | 500 Hz | 100 µs | 100 ns | 1000 | 0 s |
| ~2.5% | 300 Hz | 83 µs | 10 ns | 8300 | 0 s |
| ~1% | 200 Hz | 50 µs | 250 ns | 200 | 0 s |
| ~0.5% | 50 Hz | 100 µs | 50 ns | 1000 | 50 ns |
| ~0.25% | 250 Hz | 10 µs | 10 ns | 1000 | 0 s |
| ~0.1% | 20 Hz | 50 µs | 10 ns | 2500 | 10 ns |
| ~0.01% | 10 Hz | 10 µs | 20 ns | 500 | 0 s |

A low duty-cycle cutting pulse waveform may be used for cutting tissue, particular biological tissue. In some variations, the low duty-cycle cutting pulse waveform has a duty cycle of less than 2.5% (e.g., between about 2.5% and 0.1%). For example, relatively dry skin may be cut using an elongated electrode having an exposed edge (or a wire electrode, as described above) at a low duty-cycle of approximately 2% (e.g., minipulse burst duration of 75 µs, minipulse duration of 250 ns, a rep rate of 200 Hz, and a voltage of approximately ±425 V).

As described above, there is a relationship between the length or size of the electrode and the ability to cut at low duty-cycle. For example, longer or wider electrodes may require more energy to initiate and maintain plasma for cutting. The examples provided herein may be used with any relatively long (e.g., less than 5 mm long) electrode. In operation, the duty-cycle (or relevant parameters affecting the duty-cycle such as the rep rate of the burst of minipulses, the duration of the burst of minipulses, the duration of the minipulses, the voltage of the minipulses, the intraburst interval of the minipulses, or the number of minipulses) may be ns-100 ns). In some variation, the voltage of the minipulses is selectable within a range, e.g., ±600V). In some variations, the intraburst interval of the minipulses is selectable within a range, e.g., 0 s-100 ns. In some variations, the number of minipulses within a burst is selectable within a range, e.g., 100-10000. The voltage controller may include any combination of these controls to achieve the cutting pulse waveform.

Figure 14A:
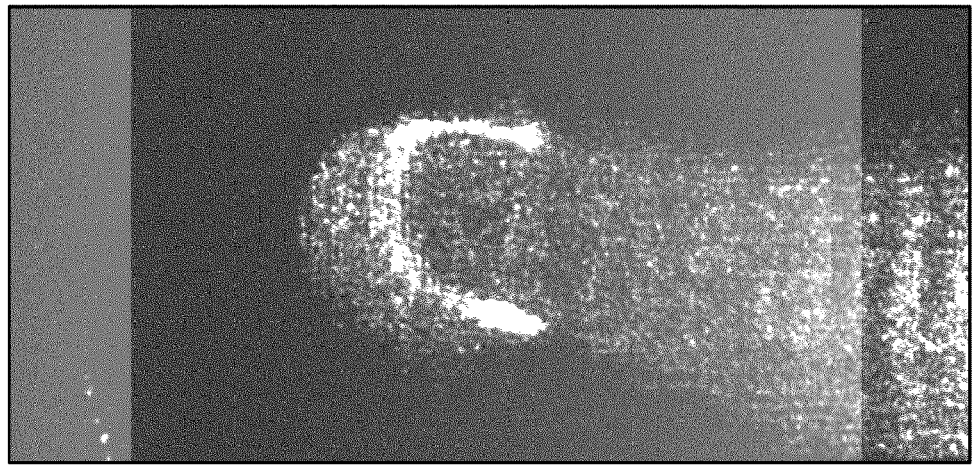
FIGS. 14A-14C illustrate heat patterns of cutting electrodes under different pulsing regimes.
Figure 14B:
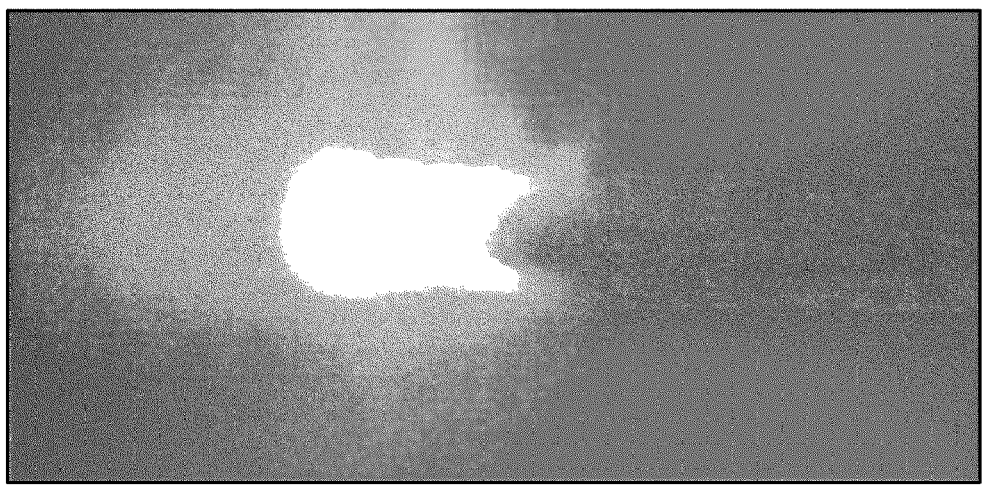
Figure 14C:
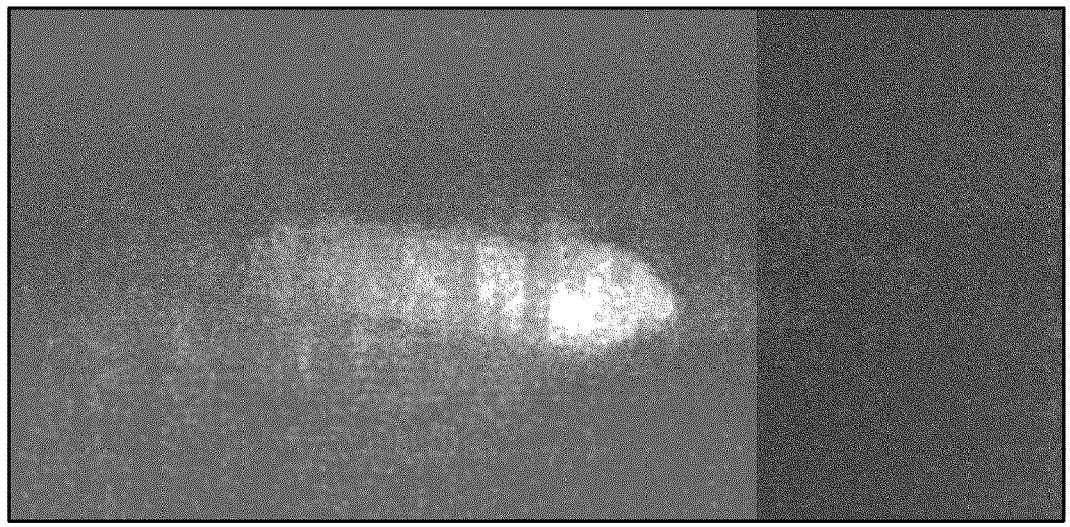

One consequence of the low-duty cycle pulse waveform is that the average temperature of the cutting electrode (and particularly the temperature of the exposed, or uninsulated cutting region) is substantially lower than cutting electrodes driven by non-low duty-cycle pulse waveforms, or driven by continuous RF energy. Examples of this are shown in FIG. 14A-14C, which show thermal images of electrodes driven by different stimulation regimes (including pulse waveforms). The temperature of the region imaged in FIGS. 14A-14C roughly corresponds to the light intensity in the images.

FIG. 14A shows a cutting electrode having a curved edge that is uninsulated during the application of a cutting pulse waveform having a duty cycle of approximately 1%. By examining thermal images such as this one, it was determined that the average temperature over the cutting edge of the cutting electrode during application of a low duty-cycle pulse waveform was approximately 37° C. FIG. 14B shows another cutting electrode (e.g., a ValleyLab™ "electrosurgical pencil") driven by a continuous RF waveform at relatively low power (e.g., 30 W). As the thermal image in FIG. 14B illustrates, the average temperature over the cutting portion of the electrode is much higher, and in this example was greater than 300° C. FIG. 14C shows another example of an electrode (Arthrocare™ TurboVac at set point 8, approximately 300 Volts) in which the average temperature of the electrode is 110° C. In FIGS. 14A-14C, the ambient temperature of the tissue was below 37° C. (e.g., the tissue was chilled).

Although the average temperature of the cutting electrode during the application of a low duty-cycle pulse waveform may be significantly less than 100° C., the instantaneous temperature at the cutting edge may be much greater than 100° C., as described above. Under the pulse waveforms descried herein, formation of plasma (e.g., formation of a vapor cavity, ionization, etc.) may result in very high temperatures (much greater than 100° C.) during a portion of the minipulse burst. However, at low duty cycles the pulse waveform comprises a burst of minipulses separated by an inter-burst interval (rep rate) that is sufficiently long to allow the temperature at the edge of the electrode to relax back down, preventing sustained heating of the electrode while allowing cutting via. the plasma.

Thus, in some variations, the pulse waveform selected to be applied may be selected based on the average temperature. For example, thermo-electrical cutting of biological tissue may be performed by applying a low duty-cycle pulse waveform to a cutting electrode wherein the cutting electrode has an average temperature during application of the pulse waveform of less than about 50° C. (when the temperature of the tissue is initially at approximately 37° C. or cooler). The peak temperature during application of this pulse waveform may be greater than 100° C. In some variations, the average temperature during application of the pulse waveform is less than about 40° C.

The apparatus and method of the invention ensure efficient thermal ablation at low power levels, e.g., ranging down to 10 mW by overheating and evaporation. Devices built in accordance with the invention can be used for cutting various types of materials including biological tissue while minimizing the damage zone and heat accumulation in the material being cut as well as the surroundings and the hand piece. The voltages necessary for producing the plasma are reduced significantly in comparison to prior art devices. Because of such power efficiency and low thermal damage the apparatus of invention and method for operating it can be adapted to numerous applications in surgery on very sensitive organs, such as the eye. For example, the apparatus of invention can be used for: (a) dissection of membranes and cutting retina in vitreoretinal surgery, (b) capsulotomy, (c) lensectomy, (d) iridectomy, (e) trabeculectomy.

As mentioned briefly above, the apparatus and methods described herein may also be used for some blood control or hemostatis. For example, in addition to (or instead of) cutting or ablating tissue, the electrode (cutting electrode) may be used to prevent blood loss by not only cauterizing blood vessels, but also constricting them with very little thermal damage. Thus the described methods may be methods of preventing blood loss by applying a pulse waveform having a duty-cycle of less than 10% to a cutting electrode, as described herein.

Figure 15A:
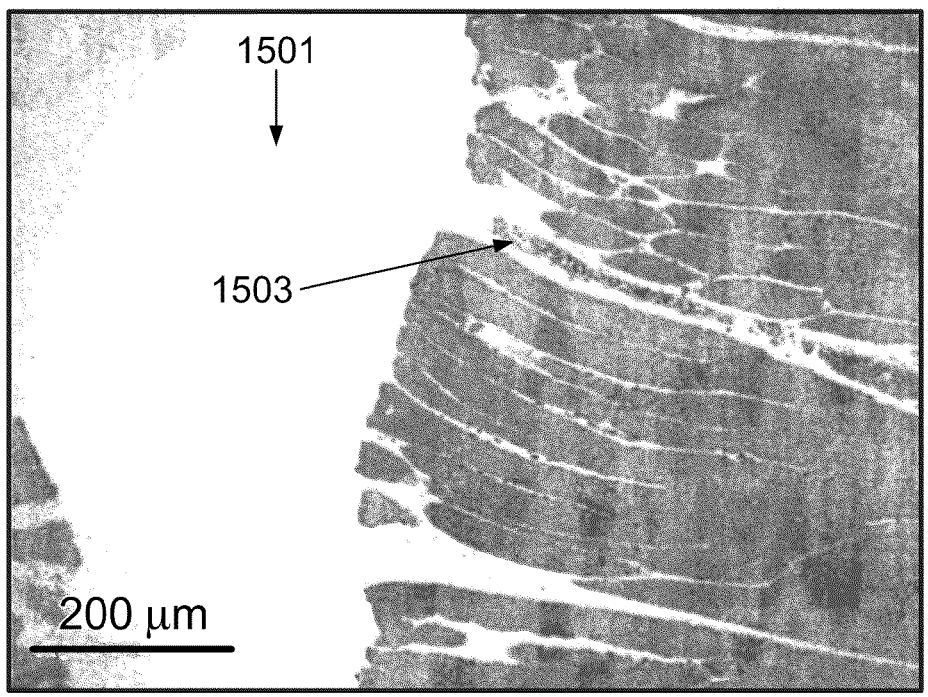
FIGS. 15A and 15B are sections through tissue cut using a cutting electrode and a low duty-cycle pulse waveform.
Figure 15B:
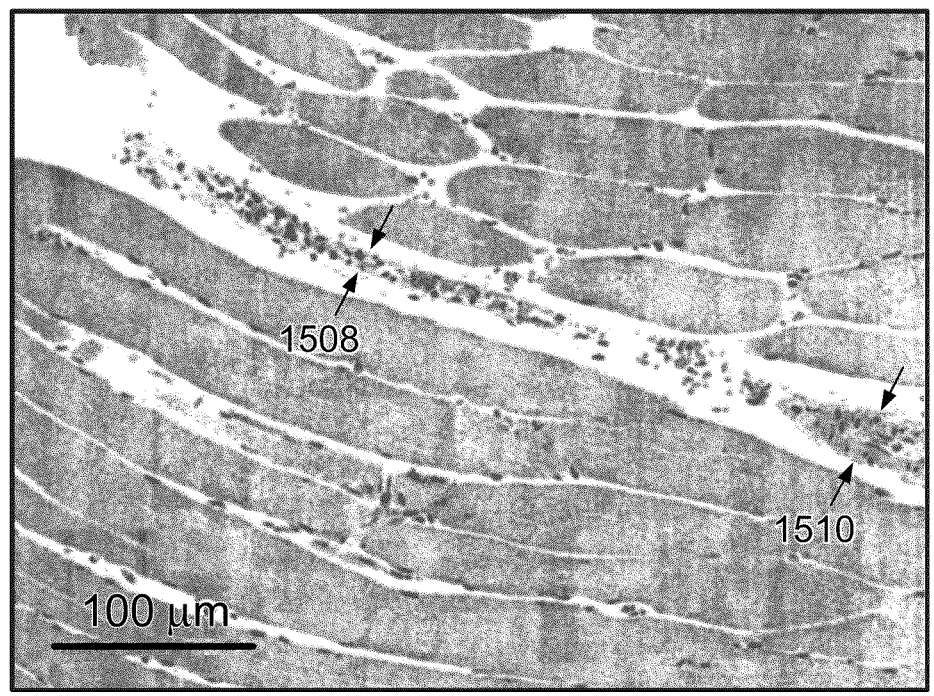

FIGS. 15A and 15B are sections through tissue cut using a cutting electrode and the low duty-cycle pulse waveform described above, and illustrates the hematostatic effect of the low duty-cycle cutting on vessels adjacent to the cut. In particular, FIGS. 15A and 15B show CAM (chick chorioallantoic membrane) tissue that was cut by a low duty-cycle waveform (with a 300 Hz rep rate, having bursts of minipulses of approximately 200 minipulses at ±450V). In FIG. 15A, the tissue has been cut 1501, so that at least one blood vessel 1503 was been severed. FIG. 15B shows a magnified view of this blood vessel 1503. The severed blood vessel is substantially constricted for a short distance from the region of the cut 1501, as indicated by the space between the arrows 1508. Thus, the internal lumen of the blood vessel has been reduced to a diameter of less than about 15 µm. Further along the length of the vessel away from the cut 1501, the blood vessel has a more normal diameter, 1510 (e.g., greater than 40 µm). This vasoconstriction results in a reduction or elimination of bleeding from the cut vessel, and appears in both arteries and veins cut by the low duty-cycle cutting waveform.

A similar hematostatic effect of electrical energy applied to tissue is described in PCT application WO PCT/US2005/033856, filed Sep. 20, 2005 (titled "METHODS AND DEVICES FOR THE NON-THERMAL, ELECTRICALLY-INDUCED CLOSURE OF BLOOD VESSELS"), herein incorporated by reference in its entirety. This effect of low duty-cycle cutting is particularly surprising and unexpected, and may provide the cutting methods and devices described herein with unexpected advantages. The effect does not appear to be dependent on thermal coagulation. As described above, the average temperature of a cutting electrode stimulated by a low duty-cycle pulse waveform is relatively low. Thus, there may be less thermal damage. Although the biological mechanism behind the hemostatic effect is not completely understood, it may be related to calcium ion channels, since calcium channel agonists may at least partly inhibit this effect.

Thus, when cutting tissue using any of the cutting electrodes described above using any of the low duty-cycle pulse waveforms described, bleeding may be substantially reduced by the non-thermal hematostatis (or "non-thermal coagulation"). FIG. 16A is a graph comparing bleeding from a cutting electrode using a low duty-cycle pulse waveform to a scalpel (blade), and to a high voltage, high duty-cycle device control (Control 1) that cauterizes as it cuts. In this example, porcine tissue was cut (e.g., porcine skin and muscle tissue) with a scalpel, a control electrosurgical device operating under continuous RF stimulation (100% duty cycle), and with a cutting electrode operating on a low duty-cycle. The control 1 (100% duty cycle) device was a ValleyLab™ "electrosurgical pencil" operating at 40 W in the fulguration mode. The low duty-cycle waveform had a rep rate 200 Hz with burst of approximately 200 minipulses per burst, and a voltage of ±425V. As shown in FIG. 16A, the cutting electrode using a low duty-cycle pulse waveform bleeds less than a comparable cut made by a scalpel. In this example the low duty-cycle cut bled approximately 71.3% less bleeding than scalpel (N=3, p=0.003). Although cauterization using a traditional electrosurgical device (e.g., the control 1 device), thermal cauterization may also result in substantially more tissue damage, and may promote scar formation. FIG. 16B shows a graph illustrating wound strength for cuts similar made with the low duty-cycle cutting electrode 1610 (diamonds), a thermally cauterizing cutting electrode 1612 (squares), and a scalpel 1614 (triangles).

In FIG. 16B, wound strength is measured at different times after a cut was made. In this example, comparable cuts were made in porcine skin tissue using either a cutting electrode under a low duty-cycle pulse waveform, a scalpel, or a cauterizing electrosurgical device (driven by a continuous RF waveform). Wound strength was measured 1 week after a cut, 2 weeks after a cut, 3 weeks after a cut, and six weeks after a cut. Cuts were approximately 2 cm long. Tissue strength was determined using a tensile tester applied across the cut tissue after it had healed for the indicated amount of time, and force was applied until separation. As FIG. 16B shows, the wound strength of the cut formed by the low duty-cycle cut is comparable to that formed by the scalpel, and both are slightly stronger than the thermally cauterized cut at each time point measured (thermal cuts are approximately 60% less strong than scalpel and low duty-cycle cuts). Although such results may vary depending on the size and location of the cut made, as well as the type of tissue, such results are highly suggestive that low duty-cycle cutting by a cutting electrode may both inhibit bleeding and may promote healing.

The above detailed description is provided to illustrate exemplary embodiments and is not intended to be limiting. For example, any of the features of an embodiment may be combined with some or all of the features of other embodiments. It will be apparent to those skilled in the art that numerous modifications and variations within the scope of the present invention are possible. Throughout this description, particular examples have been discussed, including descriptions of how these examples may address certain disadvantages in related art. However, this discussion is not meant to restrict the various examples to methods and/or systems that actually address or solve the disadvantages. Accordingly, the present invention is defined by the appended claims and should not be limited by the description herein.

What is claimed as new and desired to be protected by Letters Patent of the United States is:

1. A method for thermo-electrical cutting of biological tissue comprising:
    applying a low duty-cycle pulse waveform to a cutting electrode, wherein the cutting electrode has a peak temperature during application of the pulse waveform of greater than 100° C. and an average temperature during application of the pulse waveform of less than about 50° C.; and
    cutting the tissue with the cutting electrode during application of the low duty-cycle pulse waveform.

2. The method of claim 1, wherein applying the low duty-cycle cutting waveform comprises applying a plurality of pulses having a duty cycle of less than 10%.

3. The method of claim 1, wherein applying the low duty-cycle cutting waveform comprises applying a plurality of pulses having a duty cycle of less than 5%.

4. The method of claim 1, wherein applying the low duty-cycle cutting waveform comprises applying a plurality of pulses having a duty cycle of between about 2.5% and about 0.01%.

5. The method of claim 1, wherein applying the low duty-cycle cutting waveform comprises applying a plurality of pulses wherein each pulse comprises a burst of minipulses.

6. The method of claim 5, wherein the minipulses within the burst of minipulses comprise bipolar minipulses.

7. The method of claim 5, wherein the duration of each minipulse within the burst of minipulses is between about 10 ns and about 100 µs.

8. The method of claim 5, wherein the minipulses within each burst of minipulses are continuously applied.

9. The method of claim 1, wherein applying the low duty-cycle cutting waveform comprises applying a plurality of bursts of minipulses having an interburst repetition rate of between about 10 Hz and 500 Hz, and a minipulse burst duration of between about 5 µs and about 200 µs.

10. The method of claim 1, wherein applying the low duty-cycle cutting waveform comprises applying a plurality of pulses having a voltage of between about −500 V and about +500 V.

11. The method of claim 1, wherein the average temperature of the cutting electrode during application of the pulse waveform is less than about 40° C.

12. A method of simultaneously cutting and hemostasis of a biological tissue, the method comprising:
    contacting a biological tissue with a cutting electrode,
    applying a low duty-cycle pulse waveform to the cutting electrode, wherein the cutting electrode has a peak temperature during application of the pulse waveform of greater than 100° C. and an average temperature during application of the pulse waveform of less than about 50° C.; and
    cutting the tissue with the cutting electrode during application of the low duty-cycle pulse waveform while at least partially constricting the blood vessels adjacent to the cut tissue.

13. The method of claim 12, wherein applying the low duty-cycle cutting waveform comprises applying a plurality of pulses having a duty cycle of less than 10%.

14. The method of claim 12, wherein applying the low duty-cycle cutting waveform comprises applying a plurality of pulses having a duty cycle of less than 5%.

15. The method of claim 12, wherein applying the low duty-cycle cutting waveform comprises applying a plurality of pulses wherein each pulse comprises a burst of minipulses.

16. The method of claim 15, wherein the minipulses within the burst of minipulses comprise bipolar minipulses.

17. The method of claim 15, wherein the duration of each minipulse within the burst of minipulses is between about 10 ns and about 100 µs.

18. The method of claim 15, wherein the minipulses within each burst of minipulses are continuously applied.

19. The method of claim 12, wherein applying the low duty-cycle cutting waveform comprises applying a plurality of bursts of minipulses having an interburst repetition rate of between about 10 Hz and 500 Hz, and a minipulse burst duration of between about 5 µs and about 200 µs.

20. The method of claim 12, wherein applying the low duty-cycle cutting waveform comprises applying a plurality of pulses having a voltage of between about −500 V and about +500 V.

21. The method of claim 12, wherein the average temperature during application of the pulse waveform is less than about 40° C.

* * * * *

UNITED STATES PATENT AND TRADEMARK OFFICE
CERTIFICATE OF CORRECTION

| | | |
|---|---|---|
| PATENT NO. | : 8,043,286 B2 | Page 1 of 1 |
| APPLICATION NO. | : 11/784382 | |
| DATED | : October 25, 2011 | |
| INVENTOR(S) | : Palanker et al. | |

It is certified that error appears in the above-identified patent and that said Letters Patent is hereby corrected as shown below:

In the Specification Under Column 1:

• Please replace Column 1, line no. 16-21 with:

-- FEDERALLY-SPONSORED RESEARCH OR DEVELOPMENT
This invention was made with Government support under contract EY012888 awarded by the National Institutes of Health. The Government has certain rights in this invention. --

Signed and Sealed this
Fifteenth Day of January, 2013

David J. Kappos
*Director of the United States Patent and Trademark Office*